United States Patent
Park et al.

(10) Patent No.: US 9,109,045 B2
(45) Date of Patent: Aug. 18, 2015

(54) MASS PRODUCING GROWTH FACTOR USING ADIPOSE DERIVED ADULT STEM CELLS

(75) Inventors: ByungSoon Park, Seoul (KR); BongGeun Choi, Seoul (KR); ChulHong Park, Seoul (KR)

(73) Assignees: Byungsoon Park, Seoul (KR); PROSTEMICS CO., LTD., Seoul (KR)

( * ) Notice: Subject to any disclaimer, the term of this patent is extended or adjusted under 35 U.S.C. 154(b) by 1468 days.

(21) Appl. No.: 12/161,899

(22) PCT Filed: Oct. 12, 2006

(86) PCT No.: PCT/KR2006/004111
§ 371 (c)(1),
(2), (4) Date: Jul. 23, 2008

(87) PCT Pub. No.: WO2007/086637
PCT Pub. Date: Aug. 2, 2007

(65) Prior Publication Data
US 2009/0004160 A1    Jan. 1, 2009

(30) Foreign Application Priority Data
Jan. 27, 2006 (KR) .................. 10-2006-0008874

(51) Int. Cl.
| | |
|---|---|
| C12N 5/00 | (2006.01) |
| C07K 14/50 | (2006.01) |
| C07K 14/495 | (2006.01) |
| C07K 14/52 | (2006.01) |
| C12N 5/0775 | (2010.01) |

(52) U.S. Cl.
CPC ............. *C07K 14/503* (2013.01); *C07K 14/495* (2013.01); *C07K 14/52* (2013.01); *C12N 5/0667* (2013.01); *C12N 2500/02* (2013.01); *C12N 2500/38* (2013.01); *C12N 2500/60* (2013.01); *C12N 2500/99* (2013.01); *C12N 2510/02* (2013.01)

(58) Field of Classification Search
CPC .... C07K 14/495; C07K 14/503; C07K 14/52; C12N 2500/02
See application file for complete search history.

(56) References Cited

U.S. PATENT DOCUMENTS

| | | | |
|---|---|---|---|
| 6,372,494 B1 | 4/2002 | Naughton et al. | |
| 2005/0076396 A1 * | 4/2005 | Katz et al. ............... | 800/8 |
| 2005/0250202 A1 | 11/2005 | March et al. | |
| 2007/0292400 A1 | 12/2007 | Lipton et al. | |
| 2008/0213198 A1 * | 9/2008 | Lintner et al. .................. | 424/59 |

FOREIGN PATENT DOCUMENTS

| | | |
|---|---|---|
| WO | WO 00/24378 | 5/2000 |
| WO | WO 03/022988 | 3/2003 |
| WO | WO 03/059272 | 7/2003 |
| WO | WO 03/084468 | 10/2003 |
| WO | WO 2005/042730 | 5/2005 |

OTHER PUBLICATIONS

Longo et al (JBC, 277(41): 38239-38244, 2002).*
Assouline, et. al., "In vivo binding of topically applied human bFGF on rabbit corneal epithelial wound" In Growth Factors (1989), vol. 1(3) 251-261.
Claffey, et al., "Vascular Endothelial Growth Factor Regulation by cell differentiation and activated second messenger" In J. Biol. Chem (Aug. 1992), vol. 267(23) 16317-16322.
McPherron, et al., "GDF-3 and GDF-9 Two New Members of the Transforming Growth Factor-β Superfamily Containing a Novel Pattern of Cysteines" In J. biol. Chem. (Feb. 1993), vol. 268(5) 3444-3449.
Rehman, et al., "Secretion of Angiogenic and Antiapoptotic Factors by Human Adipose Stromal Cells", In Circulation (2004), vol. 109 1292-1298.
Fraser, et al., "Fat Tissue an Underappreciated Source of Stem Cells for Biotechnology", In Trends In Biotechnology (Apr. 2006), vol. 24(4) 150-154.
Rehman et al., "Secretion of Angiogenic and Antiapoptotic Factors by Human Adipose Stromal Cells", Circulation, 2004;109:1292-1298.
Nakagami, et al., "Novel Autologous Cell Therapy in Ischemic Limb Disease Through Growth Factor Secretion by Cultured Adipose Tissue-Derived Stromal Cells", Arter., Throm., and Vasc. Biol., (Jan. 2005), vol. 25(12) 2542-2547.
Rehman, et al., "Angiogenic Potential of Subcutaneous Adipose Stromal Cells for Autologous Cell Therapy", Jour. Amer. College of Cardiol., (Mar. 2003) vol. 41(6), Suppl. A.
Nakagami, et al., "Adipose Tissue-Derived Stromal Cells as a Novel Pption for Regenerative Cell Therapy." Jour. of Ather. And Throm., (Apr. 2006), vol. 13(2), 77-81.
Fitzpatrick, R.E. et al., "Reversal of photodamage with topical growth factors: a pilot study," J. Cosmetic & Laser Ther., 2003, 5:25-34.

* cited by examiner

*Primary Examiner* — Deborah Crouch
*Assistant Examiner* — Magdalene Sgagias
(74) *Attorney, Agent, or Firm* — Mintz Levin Cohn Ferris Glovsky and Popeo, P.C.; Kongsik Kim

(57) ABSTRACT

The present invention relates to a method for producing large amounts of human growth factors from human adipose-derived stem cells. More specifically, the invention provides a method capable of synthesizing human growth factors in significantly large amounts by culturing adipose-derived stem cells extracted from human adipose cells in suitable media and conditions. Also, stem cell culture media produced according to the method of the invention, and human growth factors isolated from the culture media, can be advantageously used as raw materials for drugs and cosmetics.

3 Claims, 10 Drawing Sheets after application

```
                        SEQUENCE LISTING

<160> NUMBER OF SEQ ID NOS: 11

<210> SEQ ID NO 1
<211> LENGTH: 20
<212> TYPE: DNA
<213> ORGANISM: Artificial Sequence
<220> FEATURE:
<223> OTHER INFORMATION: Forward primer for VEGF

<400> SEQUENCE: 1
tacctccacc atgccaagtg                                                  20

<210> SEQ ID NO 2
<211> LENGTH: 21
<212> TYPE: DNA
<213> ORGANISM: Artificial Sequence
<220> FEATURE:
<223> OTHER INFORMATION: Reverse primer for VEGF

<400> SEQUENCE: 2
tgatgattcd tgccctcctc c                                                21

<210> SEQ ID NO 3
<211> LENGTH: 17
<212> TYPE: DNA
<213> ORGANISM: Artificial Sequence
<220> FEATURE:
<223> OTHER INFORMATION: Forward primer for bFGF

<400> SEQUENCE: 3
gacggcagag ttgacgg                                                     17

<210> SEQ ID NO 4
<211> LENGTH: 26
<212> TYPE: DNA
<213> ORGANISM: Artificial Sequence
<220> FEATURE:
<223> OTHER INFORMATION: Reverse primer for bFGF

<400> SEQUENCE: 4
ctctctcttc tgcttgaagt tgtagc                                           26

<210> SEQ ID NO 5
<211> LENGTH: 21
<212> TYPE: DNA
<213> ORGANISM: Artificial Sequence
```

```
<220> FEATURE:
<223> OTHER INFORMATION: Forward primer for TGFb-1

<400> SEQUENCE: 5
gctgagcgct tttctgatcc t                                              21

<210> SEQ ID NO 6
<211> LENGTH: 21
<212> TYPE: DNA
<213> ORGANISM: Artificial Sequence
<220> FEATURE:
<223> OTHER INFORMATION: Reverse primer for TGFb-1

<400> SEQUENCE: 6
cgagtgtgct gcaggtagac a                                              21

<210> SEQ ID NO 7
<211> LENGTH: 482
<212> TYPE: DNA
<213> ORGANISM: Homo sapiens

<400> SEQUENCE: 7
tgctggtgat gggagttgta ttttcagtct tcgccaggtc attgagatcc atccactcac     60
atcttaagca ttcttcctgg caaaaattta tggtgaatga atatggcttt aggcggcaga    120
tgatatacat atctgacttc ccaaaagctc caggatttgt gtgctgttgc cgaatactca    180
ggacggacct gaattctgat tttataccag tctcttcaaa aacttctcga accgctgtgt    240
ctcctacgta aaaaagagag tgtacaaatc aataataatt acactttag aaactgtatc     300 atcaaagatt ttcagttaaa gtagcattat gtaaaggctc aaaacattac cctaacaaag    360
taaagttttc aatacaaatt ctttgccttg tggatatcaa gaaatcccaa aatatttcct    420
taccactgta aattcaagaa gcttttgaaa tgctgaatat ttctttggct gctacttgga    480
gg                                                                   482

<210> SEQ ID NO 8
<211> LENGTH: 343
<212> TYPE: DNA
<213> ORGANISM: Homo sapiens

<400> SEQUENCE: 8
tacctccacc atgccaagtg gtcccaggct gcacccatgg cagaaggagg agggcagaat     60
catcacgaag tggtgaagtt catggatgtc tatcagcgca gctactgcca tccaatcgag    120
accctggtgg acatcttcca ggagtaccct gatgagatca gtacatctt caagccatcc     180 tgtgtgcccc tgatgcgatg cggggggctgc tgcaatgacg agggcctgga gtgtgtgccc    240
actgaggagt ccaacatcac catgcagatt atgcggatca acctcacca aggccagcac    300 ataggagaga tgagcttcct acagcacaac aaatgtgaat gca                     343

<210> SEQ ID NO 9
<211> LENGTH: 212
<212> TYPE: DNA
<213> ORGANISM: Homo sapiens

<400> SEQUENCE: 9
gctgagcgct tttctgatcc tgcatctggt cacggtcgcg ctcagcctgt ctacctgcag     60
cacactcgat atggaccagt tcatgcgcaa gaggatcgag gcgatccgcg ggcagatcct    120
gagcaagctg aagctcacca gtcccccaga agactatcct gagcccgagg aagtcccccc    180
```

```
ggaggtgatt tccatctaca acagcaccag gg                              212

<210> SEQ ID NO 10
<211> LENGTH: 20
<212> TYPE: DNA
<213> ORGANISM: Artificial Sequence
<220> FEATURE:
<223> OTHER INFORMATION: Forward primer for Collagen type I

<400> SEQUENCE: 10
ccctcaaggt ttccaaggac                                             20

<210> SEQ ID NO 11
<211> LENGTH: 20
<212> TYPE: DNA
<213> ORGANISM: Artificial Sequence
<220> FEATURE:
<223> OTHER INFORMATION: Reverse primer for Collagen type I

<400> SEQUENCE: 11
accaggttca cccttcacac                                             20
```

MASS PRODUCING GROWTH FACTOR USING ADIPOSE DERIVED ADULT STEM CELLS

CROSS-REFERENCES TO RELATED APPLICATIONS

This application is a U.S. national phase application, pursuant to 35 U.S.C. §371, of PCT/KR2006/004111, filed Oct. 12, 2006, designating the United States and published on Aug. 2, 2007 as WO 2007/086637 A1, which claims priority to Korean application 10-2006-0008874, filed Jan. 27, 2006. The entire contents of the aforementioned patent applications are incorporated herein by this reference.

TECHNICAL FIELD

The present invention relates to a method for producing large amounts of growth factors from human adipose-derived stem cells. More specifically, the present invention provides a method which comprises culturing adipose-derived stem cells extracted from human fat cells in suitable media and conditions, such that human growth factors, for example, an acidic fibroblast growth factor (acidic FGF), a basic fibroblast growth factor (basic FGF), an insulin-like growth factor-1 (IGF-1), an insulin-like growth factor-2 (IGF-2), a keratinocyte growth factor, a platelet-derived growth factor (PDGF), a human transforming growth factor-alpha (TGF-α), a human transforming growth factor-beta (TGF-β), a vascular endothelial growth factor (VEGF), an epidermal growth factor (EGF) or a nerve growth factor, can be synthesized in amounts significantly larger than using existing methods involving stem cells.

BACKGROUND ART

As used herein, the term "stem cell" refers to a cell, which remains undifferentiated into a particular cells type, and, if necessary, has the potential to differentiate into all types of cells constituting the body, including nerve, blood, cartilage, etc. Methods capable of producing such stem cells are broadly classified into two categories: (1) a method of producing stem cells from embryos developed from fertilized eggs (embryonic stem cells); and (2) a method of recovering stem cells stored in each part of the adult human body (adult stem cells). Although embryonic stem cells and adult stem cells are functionally different from each other, they all have the ability to differentiate into various cells types.

The embryonic stem cells have advantages of very good differentiation potential and long telomeres, but have ethical problems and in the disadvantage that they are difficult to obtain in large amounts. In comparison, the adult stem cells can be obtained in large amounts, but have the disadvantage that, when these cells are transplanted into other persons, they carry the risk of infection and have a relatively low differentiation potential.

Despite the above-described disadvantages, adult stem cells are considerably safe for use in medical applications. Specifically, these cells do not cause cancer even when they are transplanted into the body for organ regeneration, and they do not cause immune rejection reactions because they have originated from one's own body. Thus, these adult stem cells can be used for autologous transplantation.

Also, the adult stem cells have site-specific differentiation potential to differentiate according to the characteristics of the peripheral tissues, and do not cause cancer even when they are injected in an undifferentiated state. Thus, these adult stem cells have the potential to produce cells immediately after transplantation and also display the self-renewal potential to create and store undifferentiated stem cells, if necessary.

Due to the above-described advantages, the importance of adult stem cells has recently been highlighted, and various studies have been conducted to obtain adult stem cells in vivo.

Adipose tissue plays an important role in normal growth and physiological action in vivo, but the importance thereof has been previously unappreciated. The most general type of fat is white adipose tissue, which is located below the skin (subcutaneous fat) in the abdominal cavity (visceral fat) or around reproductive organs (gonadal fat). Brown adipose tissue is a slightly less general form of fat present in an adult, which plays an important role in the production of heat during the infant stage (Gimble, New Biol. 2(4): 304-12, (1990)).

However, in fact, reproductive capability and stage of maturity are closely associated with adipose tissue storage in individuals. Female and male adolescence are closely associated with the production and secretion of adipose tissue-derived hormones and with body fat composition. Also, adipose tissue plays an important role in glucose metabolism and energy balance.

For a few years, there has been a significant advancement in the biomaterial field. On the basis of this, many materials are currently developed and used. Despite this progress, many studies have, in fact, not been conducted on the use of human adipose tissue. However, since it was recently reported that adult stem cells are present in adipose tissue (Zuk P A, et al., Molecular Biology of Cell, 13: 4279-4295 (2002); Rodriguez A M, et al., Biochimie, 87: 125-128 (2005)), various studies on the use of adipose-derived cells have been conducted.

Also, with the development of the fields of biochemistry and molecular biology, small amounts of signaling substances (growth factors) have recently been found in the human body, and on the basis of these findings, theories on in vivo aging have been re-established (Stanley Cohen, Nobel Lecture 1986, Dec., 8). Moreover, it has been found that the signaling substances (growth factors) decrease as age increases, and this decrease in the growth factors is closely associated with the aging of the human body (Sporn M and Roberts A, Handbook of Experimental Pharmacology, Vol. 1, Vol. 95/1, 1990, Springer-Verlag, Del., Berlin., pp. 667-698).

Thus, it has been reported that, when external growth factors are administered to the body, the aging of the body can be inhibited, and studies on special effects of these substances have been conducted (GE Pierce and TA Mustoe, Annu Rev Med, 46. 467-481 (1995)). Specifically, studies on the structure and synthesis of the signaling substances (growth factors) have been conducted, but the most of the growth factors have protein structures, which are three-dimensionally complex, thus posing various problems in chemical synthesis and significantly increasing costs for the synthesis.

Accordingly, the present inventors have conducted studies on a method of obtaining active human growth factors at low cost while maintaining the activity thereof in the human body and, as a result, paid attention to the fact that adipose-derived adult stem cells secrete growth factors (Rehman, J. et al., Circulation, 109: 1292-1298 (2004)).

However, studies on adipose-derived adult stem cells mainly relate to the use or differentiation of the cells themselves, and methods of synthesizing growth factors from these cells have not been studied.

Korean Patent Laid-Open Publication No. 2004-94910, entitled "Improved fat cell-differentiated, adipose-derived adult stem cells and the use thereof" discloses a method capable of increasing the in vivo survival rate of adipose-derived adult stem cells, but does not disclose the meaningful synthesis of growth factors. Korean Patent Laid-Open Publication No. 2005-6408, entitled "PBR ligand having function of regulating fat cell differentiation, derivative compounds thereof, and composition for regulation of fat cell differentiation, containing the same", merely discloses a method of differentiating fat cells into other particular cells.

Also, Korean Patent Laid-Open Publication No. 2005-99274, entitled "Animal serum-free medium composition for culture of human stem cells, and method for induction of differentiation into liver cells", discloses a method of differentiating human stem cells using animal serum-free medium, and Korean Patent Registration No. 484550, entitled "Method for production of cells for cell transplantation", discloses the use of stem cells for cell transplantation.

The reason that studies on the synthesis of growth factors using adipose-derived adult stem cells are insufficient is that the methods of using adult stem cells are focused on their use through differentiation into other cells and that studies on the cytological differences between stem cells are insignificant.

Also, as described above, methods for synthesizing growth factors using recombinant genetic techniques have only been studied, as disclosed in Korean Patent Registration No. 101436, entitled "Method for producing recombined human endothelial cell growth factors", Korean Patent Registration No. 62551, entitled "Method for producing human epithelial cell growth factors by genetic recombination technology", Korean Patent Laid-Open Publication No. 2003-45032, entitled "Method for producing biologically active human acidic fibroblast growth factors and use thereof for stimulation of angiogenesis".

Accordingly, the present inventors have discovered a method for producing large amounts of growth factors using adipose-derived adult stem cells and, as a result, found that adipose-derived adult stem cells obtained through the establishment of suitable culture conditions and physical and/or chemical stimulation synthesized and secreted growth factors in significantly effective amounts compared to adipose-derived adult stem cells to which specific stimulation were not applied.

It is an object of the present invention to produce large amounts of human growth factors from adipose-derived adult stem cells, the produced human growth factors having excellent in vivo activity compared to growth factors synthesized by recombinant or chemical methods.

Another object of the present invention is to provide safe and effective drugs or cosmetics containing either human growth factors produced in large amounts from adipose-derived stem cells, or culture media of the growth factors.

SUMMARY OF THE DISCLOSURE

To achieve the above objects, in one aspect, the present invention provides a method for producing large amounts of human growth factors from adipose-derived stem cells, the method comprising the steps of: (i) isolating adipose-derived adult stem cells extracted from mammalian adipose cells; (ii) optionally culturing the stem cells in a serum medium, and then subculturing the stem cells in a serum-free medium; (iii) applying, to the adipose-derived stem cells, at least one physical stimulation selected from among low-oxygen culture, UV irradiation, nutrient deficiency and mechanical friction; and (iv) optionally adding, to the culture media, one or more vitamins selected from among vitamin A, vitamin B, vitamin C and vitamin D, wherein step (iii) and step (iv) are performed in conditions where the highest production of the human growth factors occurs.

In another aspect, the present invention provides a functional cosmetic composition containing human growth factors produced by said method.

In still another aspect, the present invention provides a functional cosmetic composition containing an adipose-derived adult stem cell culture medium obtained by said method.

According to the present invention, it is possible to produce human growth factors in large amounts from adipose-derived adult stem cells. It was found that the growth factors produced using the inventive production method had excellent safety and activity compared to those of growth factors produced according to existing production methods. Furthermore, the growth factors produced using the inventive production method could act in the same fashion as the existing growth factors of the human body. Also, it is expected that a culture medium of adipose-derived stem cells and growth factors isolated from the culture medium can be advantageously applied in drugs, quasi drugs and cosmetics for anti-wrinkle, wound healing, and scar removing.

DETAILED DESCRIPTION

Figure 1:
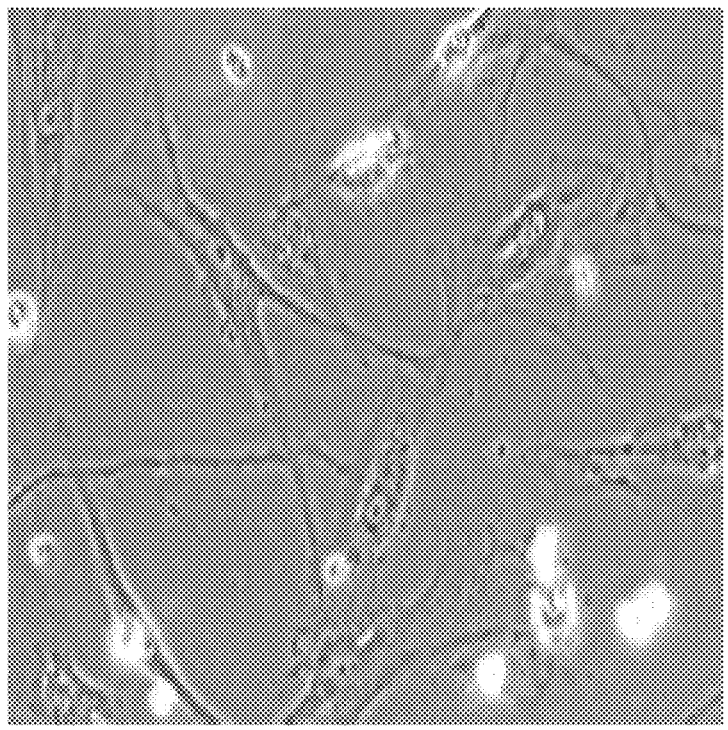
FIG. 1 is an optical microscope image of stem cells isolated from adipose tissue.

The first aspect of the present invention relates to a method for producing large amounts of growth factors using adipose-derived stem cells.

A growth factor contained in adipose-derived stem cells is selected from the group consisting of an acidic fibroblast growth factor (acidic FGF), a basic fibroblast growth factor (basic FGF), an insulin-like growth factor-1 (IGF-1), an insulin-like growth factor-2 (IGF-2), a keratinocyte growth factor (KGF), a platelet-derived growth factor (PDGF), a human transforming growth factor-alpha (TGF-α), a human transforming growth factor-beta (TGF-β), a vascular endothelial growth factor (VEGF), an epithelial growth factor (EGF), a nerve growth factor (NGF), and mixtures thereof.

In the present invention, adipose-derived stem cells were used to specifically stimulate the synthesis of the following growth factors.

1) Basic Fibroblast Growth Factor (Hereinafter, Referred to as "bFGF")

bFGF or heparin-binding growth factor 2 (HBGF-2) includes seven kinds of factors having a homology of about 30-50% at the amino acid sequence level (Burgess, W. H and Maciag, T., Annu. Rev. Biochem., 58: 575-606 (1989); Baird, A. and Klagsbrun, M., Cancer Cells, 3(6): 239-43 (1991)). bFGF is isolated from nerve tissue, the pituitary body, the adrenal cortex, corpora leutea, and the placenta.

bFGF isolated from the body has a size of about 18 kDa. Several studies have reported the existence of larger species of bFGF having a size of about 24 kDa, which result from the extension of the amino terminal end of the protein due to translation initiation at a region containing no AUG start codon (Burgess, W. H and Maciag, T., Annu. Rev. Biochem., 58: 575-606 (1989); Baird, A. and Klagsbrun, M., Cancer Cells, 3(6): 239-43 (1991); Prats, H. et al., PNAS, 86: 1836-1840 (1989); Quarto, N. et al., J. Cell. Physiol., 147(2): 311-8 (1991); Bugler, B. et al., Mol. Cell. Biol., 11(1): 573-7 (1991)). Such phenomena result in the localization of bFGF in cell nuclei rather than cytoplasm (Quarto, N. et al., J. Cell. Physiol., 147(2): 311-8 (1991); Bugler, B. et al., Mol. Cell. Biol., 11(1): 573-7 (1991)). bFGF proteins produced by general recombinant or chemical methods are based on a 18-kDa region. Production of recombinant of synthetic bFGF differs from naturally-produced bFGF, because recombinant or synthetic bFGF morphologically lacks a hydrophobic signal peptide base sequence (Mignatti, P. et al., Proc. Natl. Acad. Sci. USA 88: 11007 (1991)).

2) Vascular Endothelial Growth Factor (Hereinafter, Referred to as "VEGF")

VEGF (Ferrara, N. and Henzel, W. J. Biochem Biophys Res Commun, 161(2): 851-8 (1989)) is known as a vascular permeable factor (Senger, D. R. st al., Science, 219(4587): 983-5 (1983)), is a homodimer, has a molecular weight of 34-42 kDa, and is a heparin-bound glycoprotein. This protein has activity as an angiogenesis factor, and thus can promote the mitosis of epithelial cells and improve vascular permeability.

VEGF is expressed as a primary structure known as a limited base sequence and has homology with the A and B chains of a platelet-derived growth factor (PDGF). Such growth factors have eight conserved cysteine residues, which are involved in forming interior and solvent exposed disulfide bonds. cDNA encoded by the VEGF protein has 53% homology to the platelet-derived growth factor (PDGF) at the amino acid sequence level. VEGF was isolated from a cDNA library of the human placenta (Maglione, D. et al., PNAS, 88: 9267 (1991)). This protein is called "placenta growth factor" (PGF), and is currently recognized as a member of the VEGF family. Based on homology with VEGF, the placenta growth factor (PGF) is suggested to be an angiogenesis factor.

Genes for the human VEGFs are combined in eight exons. Alternative splicing yields base sequences of 121, 165, 189 and 206 amino acids, which encode four monomeric VEGFs. Each of the base sequences has 26 signal peptide amino acid residues, and thus can be detected. VEGF121 and VEGF165 are diffusible proteins exposed to extracellular matrixes, and VEGF189 and VEGF206 have high affinity for heparin, and thus form proteoglycan bonds with heparin in extracellular lipids. VEGF, which was originally described as a glycoprotein, contains an N-linked glycosylation site.

The VEGF proteins produced by general recombinant or chemical methods are based on sequences of the diffusible proteins VEGF121 and VEGF165 It was reported that the expression of recombinant human VEGF in *E. coli* was not different from original VEGF in vitro with respect to biological functions (Connolly, D. T. J. Cell. Biochem, 47(3): 219-23 (1991); Schott, R. J. and Morrow, L. A. Cardiovasc, Res., 27(7): 1155-61 (1993); Neufeld, G. et al., Prog. Growth Factor Res., 5(1): 89-97 (1994); Senger, D. R. et al., Cancer and Metastasis Reviews, 12(3-4): 303-24 (1993)).

3) Transforming Growth Factor-β (Hereinafter, Referred to as "TGF-β")

A human transforming growth factor (TGF), which is a factor that stimulates the transformation of fibroblasts differentiating into a tumor-like phenotype, consists of a mixture of two proteins TGF-α and TGF-β and is associated with tumor-inhibitory factors rather than a tumor-stimulating factors (Lawrence, D. A. Eur. Cytokine Netw, 7(3): 363-74 (1996); Cox, D. A. and Maurer, T., Clin. Immunol. Immunopathol, 83(1): 25-30 (1997); Alevizopoulos, A. and Mermod, N., Bioassays. 19(7): 581-91 (1997)).

The two molecules are members of the TGF super-family, including TGF-β1 having five kinds of bone morphogenic proteins as active and inactive substances (Kingsley, D. M., Genes Dev, 8: 133 (1994)). It is known that human TGF-β1 has a molecular weight of 25 kDa, consists of disulfide bonds and bi-glycosyl homodimers, and has a 100% conserved gene sequence among almost all mammalian species. TGF-β1 initiates intracellular signaling through the transfer of a disulfide bond from a precursor by a protease similar to subtilisin (Dubois, C. M. et al., J. Biol. Chem., 270: 10618 (1995)), and it is generally secreted as an inactive material or a composite of two (Gleizes, P-E. et al., Stem Cells, 15: 190-197 (1997)). A TGF-β1 signaling process includes two receptors (Ten Dijke, P. Curr. Opin. Cell Biol, 8(2): 139-45 (1996); Derynck, R. and Feng X. H., Biochim. Biophys. Acta 1333(2): F105-50 (1997); Padgett, R. W. et al., Bioessays, 20(5): 382-90 (1998)), and a TGF-β RII dimer as a 75-kDa ligand-binding protein has an intracellular serine-threonine kinase enzyme, which is continually activated. TGF-β RII phosphorylates the 53-kDa signaling dimer TGF-β RI through binding to TGF-β1. The phosphorylated TGF-β RI activates protein kinase and induces initiating a downstream signal via intracellular protein SMADS.

The TGF receptor involved in the signaling process is found in all cells and affects almost all physiological actions. The systematic and cell-specific activation thereof is a very complex mechanism, but shows three basic activities. TGF-β1 generally regulates the proliferation of cells such as inhibitory factors, promotes the precipitation of protein hydrolysates in addition to cell membranes by repeating the inhibition of protein degradation and the synthesis of proteins, and stimulates immune inhibitory reactions through various mechanisms.

A TGF-β1 protein produced by prior recombinant or chemical synthesis is an active protein having a size of 25 kDa, and thus shows biological activity similar to the original TGF-β1 protein in vitro, but it contains only some of the inherent properties of the TGF-β1 protein.

The method according to the first aspect of the present invention comprises the steps of: (i) isolating adipose-derived adult stem cells extracted from mammalian adipose cells; (ii) selectively culturing the stem cells in a serum medium and then subculturing the stem cells in a serum-free medium; (iii) applying, to the adipose-derived stem cells, at least one physical stimulation selected from among low-oxygen culture, UV irradiation, nutrient deficiency and mechanical friction; and (iv) selectively adding, to the culture media, at one or more vitamins selected from among vitamin A, vitamin B, vitamin C and vitamin D, wherein the step (iii) and the step (iv) are performed in conditions where the highest production of the human growth factors occurs.

Collection of Stem Cells

Adipose-derived adult stem cells according to the present invention can be collected through a purification process from cells present in adipose tissue. Preferably, human adipose-derived adult stem cells are collected, and for this purpose, adipose-derived stem cells are separated from human adipose tissue.

Adipose tissue is brown or white adipose tissue derived from subcutaneous, network membrane, intestinal, breast genital or other adipose tissue sites, and subcutaneous white adipose tissue can be conveniently obtained using liposuction.

Regarding the source of adipose tissue, it is possible to use adipose tissue discarded in the liposuction process, which is commonly performed. That is, the utility of the adipose tissue from liposuction is increased, because the need to perform invasive surgery for adipose tissue is eliminated. The separated liposuction material is washed, and only the adipose tissue is separated from the washed material. The extracellular matrix of the adipose tissue is treated with collagenase, and then centrifuged to collect a stromal vascular fraction containing a high density of stem cells. The pellets thus obtained are washed, and then passed through a cell filter to separate other tissues. Then, monocytes and cell fragments containing red blood cells are isolated from the remaining tissue using a monocyte isolation solution. The isolated monocyte cells are cultured in non-inducing media, and non-adhesive cells are removed.

Culture of Stem Cells

In the present invention, special culture media were established for the in vitro culture of the adipose-derived stem cells obtained in the above-described process.

Before the start of the cell culture, biological samples extracted from a supply source can be repeatedly washed with a wash medium containing general antibiotics to minimize the possibility of contamination in subsequent culture.

In the present invention, culture media are optimized so as to maximize the synthesis and secretion of growth factors in the adipose-derived stem cells.

Specifically, the in vitro culture of the adipose-derived stem cells is performed by culturing the cells in a serum medium and then subculturing the cells in a serum-free medium, such that the synthesis of growth factors is maximized.

The serum-containing medium for the initial cell culture is preferably a medium suitable for maintaining and storing cell types such as adipose-derived stem cells.

In the present invention, the medium is based on Dulbecco's Modified Eagle's Medium (DMEM), which is commonly used for cell culture in the art, and contains serum, which is commonly used in cell culture.

Herein, the initial medium may also be a frozen medium obtained by adding 7-10% of dimethyl sulfoxide (DMSO) thereto, and thus the stem cells can be frozen, and then, if necessary, can be thawed before use.

Regarding the serum, 0.1-20% fetal bovine serum (FBS) is preferably added to the medium. More preferably, the medium also contains antibiotic agents, antifungal agents and reagents for preventing contamination caused by the growth of mycoplasma.

Regarding the antibiotic agents, it is possible to use any antibiotic agent used in general cell culture, including penicillin-streptomycin. Regarding the antifungal agent, it is preferable to use amphotericin B, and as the mycoplasma inhibitory agent, it is preferable to use tylosin. In addition, the mycoplasma contamination can be prevented with gentamicin, ciprofloxacin, azithromycin, etc. If necessary, oxidation nutrients such as glutamine, and energy metabolites such as sodium pyruvate, can further be added to the medium.

A more preferred medium contains 1-2 mM glutamine, 0.5-1 mM sodium pyruvate, 0.1-10% FBS, 1% antibiotic (100 IU/ml)-supplemented glucose and DMEM, and is called "complete serum medium". Herein, the concentration of glucose is approximately 1 g/L to 4.5 g/L. The complete serum medium provides the storage and maintenance of adipose-derived stem cells and stable basic culture conditions in vitro and shows effective cell stabilization.

With respect to general culture conditions for the initial culture, the most suitable conditions for cell culture are applied, and thus the cell culture is performed in an incubator at humidity of 90-95% and a temperature of 35-39° C. under a condition of 5-10% $CO_2$. When the cell culture is carried out in a condition of 5-10% $CO_2$, a carbon source such as sodium bicarbonate is added to a final concentration of 0.17-0.22%.

During the initial culture stage, the tissue fragments are preferably kept attached to the bottom of the culture flask, and the growth of the cells can be promoted through short stimulation caused by treatment with trypsin-EDTA according to standard cell culture techniques.

Cumulative population doubling time is maintained until the cells being cultured in the flask reach a confluence of 75-85%. Preferably, the cells are collected at a confluence of 80% and subcultured in a serum-free medium for late-stage culture.

The present invention provides a serum-free medium for the differentiation of growth factors, which stimulates the differentiation of growth factors in adipose-derived stem cells.

The subculture process using the serum-free medium for the differentiation of growth factors is preferably performed by removing the medium from the culture, washing the flask with phosphate buffer saline, suspending the cells with trypsin-EDTA, centrifuging the cell suspension, and then washing the resulting pellets with buffer solution, wherein the washing process is repeated 2-3 times. The washed pellets are suspended in the serum-free medium developed in the present invention and are subcultured about 3 times in a cell culture flask.

The serum-free medium developed in the present invention is based on a DMEM that does not contain a pH indicator such as phenol red, and a Ham's F-12 nutrient mixture (SIGMA, Cancer Research Vol 47, Issue 1, 275-280) which is added thereto at a ratio of approximately 1: 0.5-2. Herein, it is possible to add oxidation nutrients such as L-glutamine, energy metabolites such as sodium pyruvate, and carbon sources such as sodium bicarbonate. In addition, it is possible to add not only other growth factors than the growth factors targeted in the present invention, but also growth hormones.

The inherent characteristic of the serum-free medium developed in the present invention can be seen in the Ham's F-12 nutrient mixture. In this mixture, various inorganic substances and amino acids, which help to maintain the growth and homeostasis of the cells and are involved in increasing the safety and maintenance of the cells in the late-stage culture following the initial-stage culture of the adipose-derived stem cells, vitamin nutrients, which can stimulate the higher production of growth factors selected from the adipose-derived stem cells, and other factors, are mixed with each other at a given ratio. The serum-free medium containing the Ham's F-12 mixture, established in the present invention, do not show any reduction or negative effect on the culture of the adipose-derived stem cells or the production of growth factor compared to the conditions of general serum media containing animal serum. Also, some growth factors show a higher productivity in the serum-free medium. All the components and contents of the serum-free culture medium are defined, unlike serum media having unknown components caused by the addition of serum.

This suggests that variability, which can result from animal serum present in serum media, can be minimized, and the effects of the present invention can be achieved at a low cost or about 50% compared to the prior art.

Table 1 below indicates the components and contents of the Ham's F-12 nutrient mixture contained in the serum-free medium established in the present invention.

TABLE 1

| Components | Concentration (mg/L) | Morality (mM) |
|---|---|---|
| Amino acid | | |
| D-Pantothenic Acis | 2.24 | 0.00895 |
| Glycine | 18.75 | 0.25 |
| L-Alanine | 4.45 | 0.05 |
| L-Arginine hydrochloride | 147.5 | 0.699 |
| L-Asparagine-$H_2O$ | 7.5 | 0.05 |
| L-Aspartic acid | 6.65 | 0.05 |
| L-Cysteine hydrochloride-$H_2O$ | 17.56 | 0.0998 |
| L-Cystine 2HCl | 31.29 | 0.1 |
| L-Glutamic Acid | 7.35 | 0.05 |
| L-Glutamine | 365 | 2.5 |
| L-Histidine hydrochloride-$H_2O$ | 31.48 | 0.15 |
| L-Isoleucine | 54.47 | 0.416 |
| L-Leucine | 59.05 | 0.451 |
| L-Lysine hydrochloride | 91.25 | 0.499 |
| L-Methionine | 17.24 | 0.116 |
| L-Phenylalanine | 35.48 | 0.215 |
| L-Proline | 17.25 | 0.15 |
| L-Serine | 26.25 | 0.25 |
| L-Threonine | 53.45 | 0.449 |
| L-Tryptophan | 9.02 | 0.0442 |
| L-Tyrosine disodium salt dihydrate | 55.79 | 0.214 |
| L-Valine | 52.85 | 0.452 |
| Vitamins | | |
| Biotin | 0.0035 | 0.0000143 |
| Choline chloride | 8.98 | 0.0641 |
| D-Calcium pantothenate | 2.24 | 0.0047 |
| Folic Acid | 2.65 | 0.00601 |
| i-Inositol | 12.6 | 0.07 |
| Niacinamide | 2.02 | 0.0166 |
| Pyridoxine hydrochloride | 2.031 | 0.00986 |
| Riboflavin | 0.219 | 0.000582 |
| Thiamine hydrochloride | 2.17 | 0.00644 |
| Vitamin B12 | 0.68 | 0.000502 |
| Inorganic Salts | | |
| Calcium Chloride ($CaCl_2$) (anhyd.) | 116.6 | 1.05 |
| Cupric sulfate ($CuSO_4$—$5H_2O$) | 0.0013 | 0.0000052 |
| Ferric Nitrate ($Fe(NO_2)_3 \cdot 9H_2O$) | 0.05 | 0.000124 |
| Ferric sulfate ($FeSO_4$—$7H_2O$) | 0.417 | 0.0015 |
| Magnesium Chloride (anhydrous) | 28.64 | 0.301 |
| Magnesium Sulfate ($MgSO_4$) (anhyd.) | 46.84 | 0.407 |

TABLE 1-continued

| Components | Concentration (mg/L) | Morality (mM) |
|---|---|---|
| Potassium Chloride (KCl) | 311.8 | 4.16 |
| Sodium Chloride (NaCl) | 6995.6 | 120.61 |
| Sodium Phosphate dibasic ($Na_2HPO_4$) anhydrous | 71.02 | 0.5 |
| Sodium Phosphate monobasic ($NaH_2PO_4$) anhydrous | 54.3 | 0.45257 |
| Zinc sulfate ($ZnSO_4$—$7H_2O$) | 0.432 | 0.0015 |

The components and contents of amino acids, vitamins and inorganic salts in the serum-free medium may be modified by one skilled in the art, as long as this modification does not deteriorate the object of the present invention.

To achieve the object of the present invention, it is possible to promote the synthesis of targeted growth factors by activating the adipose-derived adult stem cells cultured according to the above method, through specific stimulation. Herein, the stimulation can be performed under conditions divided into physical conditions and chemical conditions.

Examples of physical stimulations may include exposure to UV rays, nutrients, deficiency, and oxygen deficiency. Examples of chemical stimulations may include the addition of vitamins and other active compounds in the composition of a medium for cell culture.

Physical Stimulation

In order to obtain growth factors in amounts significantly larger than those in existing methods for culturing adipose-derived adult stem cells, it is possible to apply physical stimulations, including low-oxygen conditions (Circulation. 2004 Mar. 16; 109(10):1292-8.), UV irradiation (FASEB J. 2003 Mar.; 17(3):446-8), nutrient deficiency (Blood. 2004 Nov. 1; 104(9):2886-92. Epub 2004 Jun. 24), and mechanical friction. Such physical stimulations can selectively or collectively increase growth factors targeted in the present invention.

In order to examine whether physical stimulations promote the synthesis and secretion of growth factors, in the present invention, the adipose-derived stem cells were cultured in vitro using the serum medium and then using the serum-free medium as described above, the cells were then collected and the culture media were completely removed from the cells. In this state, the cells were subjected to each of low-oxygen culture, UV irradiation, nutrient deficiency and mechanical friction, and then were normally cultured, and the concentrations of growth factors secreted in the culture medium of the adipose-derived stem cells were measured.

Specifically, the low-oxygen culture is preferably performed in conditions of about 5% carbon dioxide and 1-5% oxygen for 36-48 hours for the highest synthesis of growth factors. The UV irradiation is preferably performed by irradiating ultraviolet B having a wavelength of 280-320 nm at an energy dose of 80-120 $mJ/cm^2$. The nutrient deficiency is preferably performed by culturing the cells in a $Mg^{2+}$ and $Ca^{2+}$-containing Dulbecco's phosphate buffered saline for up to a maximum of 4 hours immediately before the cells precipitate, and then normally culturing the cells in a medium obtained by adding Ham's F-12 nutrient mixture to DMEM (not containing a pH indicator such as phenol red) at a ratio of about 1:1. The mechanical friction is preferably performed by applying scratch stimulation in a lattice to the cell medium.

As a result, bFGF expression was increased 1.74 times in the case of the low-oxygen stimulation and 2.71 times in the case of the UV stimulation. Also, when the low-oxygen stimulation and the UV stimulation were performed in combination, the synergistic effect thereof was shown (see FIG. 9).

VEGF expression was increased 2.53 times in the case of the low-oxygen stimulation, 1.36 times in the case of the UV stimulation, and 1.30 times in the case of the scratch stimulation using mechanical friction. Also, when the low-oxygen stimulation, the UV stimulation and the scratch stimulation were performed in combination, the synergistic effect thereof was shown (see FIG. 10).

TGF β-1 expression was increased 1.64 times in the case of the low-oxygen stimulation, 1.75 times in the case of the UV stimulation, 2.13 times in the case of the scratch stimulation using mechanical friction, and 2.01 times in the case of the nutrient deficiency stimulation. Also, when the low-oxygen stimulation and the UV stimulation were performed in combination, the synergistic effect thereof was shown (see FIG. 11).

Chemical Stimulations

With respect to chemical conditions, it is preferable to expose a variety of generally widely known activating compounds directly or indirectly to individuals.

Activating compounds, which can be added to the adipose-derived stem cells according to the present invention, include cell aging-related retinoic acid, vinpocetine as a precursor thereof, picamillon serving as an assistant in this cycle, and quinic acid and quinate, which serve as protein kinase. In addition, carbohydrate synthesis factors, such as adenine dinucleotide and acetyl-L-carnitine, which are involved in metabolism, perform an important role in cell nutrition, and such activating compounds include other additives, such as dimethylaminoethanol, which acts to stop apoptosis, L-lipoic acid and L-hydroxy acid, which are involved in cell proliferation, and coenzyme Q-10, which is involved in amino acid production. As described above, these activating compounds can be added simultaneously or individually during the culture of the adipose-derived stem cells.

The present invention focused on the stimulatory effects of vitamin series among various activating compounds.

Generally, vitamin A is known to be involved in primary immune reactions, cell development processes related thereto, and a series of apoptosis reactions. A typical example thereof is retinoic acid, which binds to a retinoic acid receptor (RAR) to regulate and activate metabolic processes associated therewith. Among them, complexes bound to RAR-alpha, RXR-alpha and RXR-beta were reported to promote or inhibit the expression of about 128 genes, which are involved in the development of T lymphocytes as major immune cells. In particular, it was reported that bcl2 family genes known as typical anti-apoptotic proteins are definitely increased in apoptosis mechanisms (Rasooly, R. et al., J. Immunol., 175: 7916-7929 (2005); Spilianakis, C. G. et al., Eur. J. Immunol., 35(12): 3400-4 (2005); Evans T, Exp. Hematol., 33(9): 1055-61 (2005)). This suggests that vitamin A can show the effect of inhibiting apoptosis reactions.

Vitamin B is generally known as riboflavin and performs an important role in maintaining human health. One research team in Sweden reported that treatment with this substance showed an effect on neutrophil migration, thus causing an increased primary immune response (Verdrengh, M. and Tarkowski, A., Inflamm. Res., 54(9): 390-3 (2005)). It is expected that this substance can increase initial immune responses, caused by the migration of primary immune cells.

Vitamin C has important intracellular functions of promoting the synthesis of collagen and fibroblasts, and typical examples thereof include ascorbic acid. When it is used in combination with other cytokines TGF- and IFN-γ the effect thereof is further increased (Chung, J. H. et al., J. Dermatol. Sci., 15(3): 188-200 (1997)). Vitamin D3 has been frequently used, because it is known to influence cell development and differentiation, unlike other vitamins. Vitamin D3 mediates an important signaling system in cell growth and development processes, particularly formation processes of epidermal keratinocytes and osteogenic cells such as osteoblasts and osteoclasts. Also, it has an inhibitory effect against various cytokines, such as IL-1α, IL-6 and IL-8d, which are involved in inflammatory reactions (Alper, G. et al., Endocr. Rev., 23: 763 (2002)).

In the present invention, any one of or mixture of vitamin A, vitamin C and vitamin D as chemical stimulation conditions was added to culture media in an effective amount without causing cytotoxicity.

In order to examine whether chemical stimulation using a vitamin promotes the synthesis and secretion of growth factors, in the present invention, adipose-derived stem cells were cultured in vitro using serum media and then using serum-free media as described above. Then, the cells were collected and washed with phosphate buffer saline to completely remove the media, and the cells were cultured in a medium obtained by adding an Ham's F-12 nutrient mixture to a modified DMEM that did not contain a pH indicator such as phenol red, at a ratio of about 1:1, and adding thereto at least one selected from among oxidation nutrients such as L-glutamine, energy metabolites such as sodium pyruvate, and carbon sources such as sodium bicarbonate. A suitable amount of at least one vitamin selected from vitamin A, vitamin B, vitamin C and vitamin D was added to the culture medium, and then the concentrations of growth factors secreted in the culture medium of the adipose-derived stem cells were measured.

Specifically, the optimal concentration of vitamin A is 2-5 μM, the optimal concentration of vitamin B2 is 50-100 μM, the optimal concentration of vitamin C is 10-100 μM, and the optimal concentration of vitamin D is 5-10 μM. Preferably, after vitamin is added to the culture medium, the culture is incubated for more than 48 hours. When a mixture of vitamins is used, the optimal concentrations of vitamins are the same as above.

As a result, it was seen that bFGF expression was increased 1.62 times in the case of vitamin A, 1.33 times in the case of vitamin B, 2.33 times in the case of vitamin C, and 2.80 times in the case of vitamin D.

Also, it was observed that VEGF expression was increased 1.59 times in the case of vitamin A 1.68 times in the case of vitamin B, 1.68 times in the case of vitamin C, and 1.30 times in the case of vitamin D.

Moreover, it was observed that TGF β-1 expression was increased 1.20 times in the case of vitamin A, 1.56 times in the case of vitamin B, 1.20 times in the case of vitamin C, and 1.16 times in the case of vitamin D.

In addition, it was observed that, when vitamin A, vitamin B, vitamin C and vitamin D were added to the culture medium at the above-described optimal concentrations, bFGF expression was increased 3.62 times, VEGF was increased 2.03 times, and TGF β-1 was increased 1.68.

Combination of Stimulations

With respect to the case where physical stimulation was used in combination with chemical stimulation, UV light was irradiated into a culture medium, and then immediately the medium was replaced with a DMEM medium containing a Ham's F-12 nutrient mixture and optimized concentrations of vitamins A, B, C and D, and the medium was cultured in a condition of low-oxygen stimulation for the optimal culture time. In this case, bFGF expression was increased 4.11 times.

Also, VEGF expression was increased 3.92 times, when UV light was irradiated into a culture medium followed by applying scratch stimulation, and then immediately the medium was replaced with a DMEM medium containing a Ham's F-12 nutrient mixture and optimized concentrations of vitamins A, B, C and D, and the medium was cultured in a condition of low-oxygen stimulation for the optimal culture time.

Moreover, TGF β-1 expression was increased 2.35 times, when UV light was irradiated into a culture medium followed by applying scratch stimulation and nutrient deficiency, and then immediately the medium was replaced with a DMEM medium containing a Ham's F-12 nutrient mixture and optimized concentrations of vitamins A, B, C and D, and the medium was cultured in a condition of low-oxygen stimulation for the optimal culture time.

Furthermore, in order to increase the expression of bFGF, VEGF and TGF β-1, it is most preferable to use a combination of low-oxygen stimulation, UV light stimulation and vitamins A, B, C and D. Specifically, after UV light is irradiated into a culture medium, the medium is replaced with a medium containing Ham's F-12 nutrient mixture and optimized concentrations of vitamins A, B, C and D, and the medium is cultured in a condition of low-oxygen stimulation for the optimal culture time. In this case, bFGF expression is increased 4.11 times, VEGF expression is increased 3.8 times, and TGF β-1 expression is increased 1.9 times.

The second aspect of the present invention provides novel uses of a culture medium obtained using the method according to the first aspect, or human growth factors purified from the culture medium.

Specifically, adipose-derived stem cell culture media or human growth factors obtained according to the present invention can be used in drugs, quasi drugs, drug supplements, and cosmetics, which are used for anti-wrinkle, wound healing, and scar removing.

The adipose-derived stem cell culture media obtained according to the present invention include all media obtained through the following cases: i) a case in which adipose-derived stem cells are cultured in serum-free media; ii) a case in which adipose-derived stem cells were stabilized in serum media, and then cultured in serum-free media; and iii) adipose-derived stem cells were activated through physical or chemical stimulation during a culture process. Also, the human growth factors according to the present invention include all human growth factors obtained by purifying the cells or culture media obtained through the above-described culture method.

It is preferable either to use culture media obtained by culturing cells in serum media and then in serum-free media through the optimized method according to the first aspect of the present invention, or to use human growth factors purified from the said culture media.

It is more preferable either to use culture media obtained by culturing cells in serum media and then in serum-free media through the optimized method according to the first aspect of the present invention and activating the cells through physical or chemical stimulation during the culture process, or to use human growth factors purified from the said culture media.

The growth factors produced from adipose-derived adult stem cells are distinguished from growth factors synthesized through existing methods, that is, growth factors synthesized from amino acids through chemical synthesis methods, and growth factors synthesized through genetic recombinant methods.

In comparison with such growth factors synthesized by the genetic recombinant methods or the chemical synthesis methods, the growth factors produced according to the present invention have advantages in that they are structurally similar to the original growth factors of the human body, and thus have excellent skin compatibility and secured safety.

In terms of functions, the growth factors according to the present invention do not show isomerization or three-dimensional stereospecificity and have the same form as the growth factors of the body. Thus, the growth factors according to the present invention have excellent activity compared to the growth factors produced by the recombinant or chemical synthesis methods.

Specifically, fibroblast proliferation potential was compared between the growth factors of the present invention and the growth factors produced by the recombinant or chemical synthesis methods. As a result, it was seen that the growth factors produced from adipose-derived stem cells according to the present invention had excellent activity compared to the growth factors by the existing synthesis methods (see Table 5).

Also, either the adipose-derived stem cell culture media according to the present invention or human growth factors purified from the culture media have activities that increase intracellular collagen synthesis, promote fibroblast proliferation, inhibit keratinocyte proliferation caused by UV light, mitigate skin hyperkeratinization and remove wrinkles (see Tables 4, 6, 7 and 8, and FIGS. 6, 12, 13, 14, 15 and 16).

Thus, the adipose-derived stem cell culture media according to the present invention or the human growth factors purified from the culture media can be advantageously used as raw materials for drugs, quasi drugs, drug supplements and cosmetics, which are used for anti-wrinkle, wound healing, and scar removing. In particular, according to the present invention, it is possible to produce human growth factors in large amounts and to solve the prior problem of producing on ab industrial scale effective amounts of growth factors from adipose-derived adult stem cells without other operations.

Hereinafter, the present invention will be described in further detail with reference to examples. It will however be obvious to those skilled in the art that various modifications, additions and substitutions are possible, without departing from the scope and spirit of the invention as disclosed in the accompanying claims.

EXAMPLE 1

(1-1) Isolation of Adipose-derived Stem Cells

Human liposuction material collected from Leaders Clinic, Seoul, Korea was washed with an equal volume of phosphate buffer saline, and only adipose tissue was separated from the liposuction material.

The extracellular matrix of the adipose tissue was enzymatically treated with 0.075% collagenase in a 5% $CO_2$ incubator at 37° C. for 45 minutes, and the enzymatically treated adipose tissue was centrifuged at 1200 g for 5 minutes to collect a stromal vascular fraction containing a high density of stem cells. The pellets were washed with phosphate buffer saline and passed through a 70-μm nylon cell filter to remove other tissues, and only monocyte cells and cell fragments including red blood cells were separated from the remaining material using Histopaque-1077 (SIGMA).

The separated monocytes were cultured in a non-inducing medium containing Dulbecco's Modified Eagle's Medium (DMEM), 10% fetal bovine serum (FBS), 1% penicillin streptomycin and 0.17% sodium bicarbonate, in a 5% $CO_2$ incubator at 37° C. for 24 hours, and non-adhesive cells were removed therefrom, thus isolating stem cells (see FIG. 1).

(1-2) Culture of Adipose-derived Stem Cells

The initial stage culture of the stem cells isolated from the adipose tissue was performed using DMEM containing 10% FBS. Also, 1% penicillin-streptomycin (100 IU/ml, GIBCO) was added as an antibiotic agent, amphotericin B (0.5 µg/ml, Amresco) was added as an antifungal agent, tylosin (10 µg/ml, Serva, Heidelberg) was added as a mycoplasma inhibitor, and 2 mM glutamine and 1 mM sodium pyruvate were further added. The culture was conduced in a 5% $CO_2$ incubator at a humidity of 95% and a temperature of 37° C. During the 5% $CO_2$ culture, sodium bicarbonate was added at a final concentration of 0.17%.

The stem cells isolated in the above section (1-1) were suspended at a density of $10^4$ cells/ml, and 10 ml of the cell suspension was transferred and cultured in a T25 flask (area: 25 $cm^2$; volume: 50 ml) in the above-described conditions.

Cumulative doubling time was maintained until the cells being cultured in the flask reached a confluence of 80%, and the cells were subcultured at a confluence of 80%.

The flask, from which the medium had been removed, was washed with PBS, the cells were suspended with 0.25% Trypsin-EDTA (GIBCO), and the cell suspension was then centrifuged. Then, the number and viability of the cells were measured, and the cells were subcultured three times. A serum-free medium used in the subculture process was based on DMEM which did not contain a pH indicator such as phenol red, and a Ham's F-12 nutrient mixture (SIGMA) which was added thereto at a ratio of 1:1. Also, 2 mM L-glutamine and 1 mM sodium pyruvate were added to the medium, and then sodium bicarbonate was added at a concentration of 0.1 wt %. The subculture process was repeated three times.

The cell number measurement and viability examination were performed by mixing 0.1 ml of the cell suspension with the same amount of 0.2% trypan blue (SIGMA), counting stained dyed cells and non-stained cells using a hemocytometer Linder a microscope, and calculating the percentages of the stained and non-stained cells relative to the total number of the cells.

(1-3) Identification of Stem Cells

Adipose-derived stem cells express a number of adhesion and surface proteins. Regarding these proteins, SH-2, SH-3 and SH-4 monoclonal antibodies recognize the surface epitope of human mesenchymal stem cells. As a result of the analysis of peptide base sequences and absorbance, SH-3 and SH-4 were identified to be CD73 (ecto-5'-nucleotidase), and SH-2 was identified to be CD105 (endoglin). Such cell surface markers are shared by adipose-derived stem cells (Barry, F. et al., Biochem Biophys Res Commun., 289(2): 519-24 (2001)).

The confirmation of stem cells was performed by carrying out the flow cytometry of the adipose tissue-derived stem cells, cultured in the initial culture, first subculture and second subculture, using a fluorescence activated cell sorter (Beckman Coulter). Specifically, the cells were collected with 0.25% trypsin-EDTA, washed with PBS and adjusted to a cell density of $10^5$ cells/ml. Then, the cells were allowed to react with mesenchymal stem cell-specific markers CD73-PE and CD105-FITC (BD science) antibodies, and analyzed at 488 nm with an argon laser.

Figure 2:
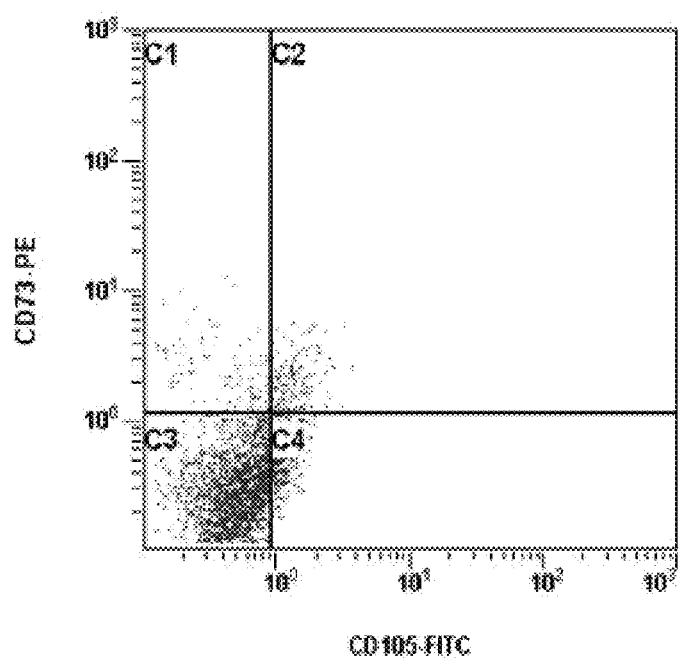
FIG. 2 shows the results of flow cytometry of originally isolated PLA cells.
Figure 3:
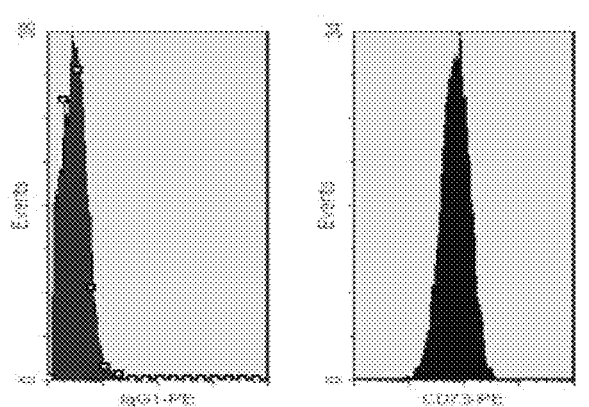
FIG. 3 is a graphic diagram showing the results of flow cytometry after subculture.
Figure 3:
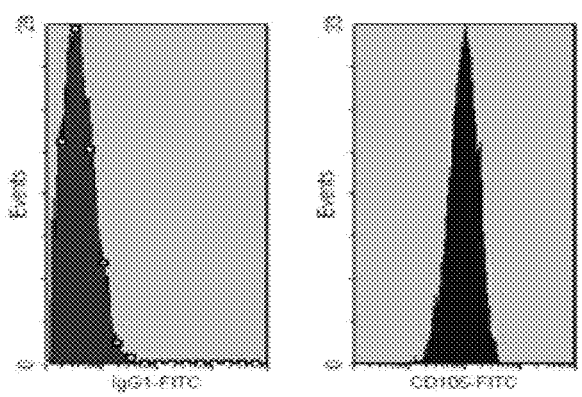

In the results of the flow cytometry of the PLA cells isolated from the adipose tissue, the initially isolated stromal vascular fraction showed a homology of 5.27% to stem cells (see FIG. 2), and after the second subculture, the cells showed a homology of 92.32% to stem cells for CD73-PE and a homology of 90.67% to stem cells for CD105-FITC (see FIG. 3).

EXAMPLE 2

Identification of Activated Growth Factors of Adipose-derived Stem Cells

In order to examine whether adipose-derived stem cells synthesize growth factors, adipose-derived stem cells were cultured in the same culture medium and culture conditions as in Example (1-2), and then RNA in the stem cells was analyzed through a reverse transcription-polymerase chain reaction.

Specifically, the total RNA of the adipose-derived stem cells was extracted with a RNeasy Plus Mini kit (QIAGEN Corp., Valencia, Calif.), and the RNA was amplified by PCR using a MMLV-reverse transferase (Promega Corp., U.S.A) at 37° C. for 45. Then, the MMLV-reverse transferase was inactivated at 65° C. for 45 minutes. The PCR reaction solution had a total volume of 50 µl and contained 1.5 mM $MgCl_2$, 0.25 mM dNTP, and 2.5 unit Taq polymerase (QIAGEN). The PCR reaction was performed in TGRADIENT (BIOMETRA) in the following conditions: a cDNA denaturation of 3 min at 94° C., and then 30 cycles each consisting of 30 sec at 94° C. (DNA denaturation), 30 sec at 60° C. (annealing) and 30 sec at 72° C. (extension), followed by a final extension of 5 min at 72° C. The reverse transcription was performed as described above to synthesize cDNA, which was then subjected to reverse transcription-PCR using primers for VEGF-β, bFGF and TGF β-1 (see Table 2).

TABLE 2

| Base sequences of primers used in RT-PCR | | |
|---|---|---|
| | Forward primer | Reverse primer |
| VEGF | 5-TACCTCCACCATGCCAAGT G-3; SEQ ID NO: 1 | 5-TGATGATTCDTGCCCTCCT CC-3; SEQ ID NO: 2 |
| bFGF | 5-GACGGCAGAGTTGACG G-3; SEQ ID NO: 3 | 5-CTCTCTCTTCTGCTTGAAG TTGTAGC-3; SEQ ID NO: 4 |
| TGFβ-1 | 5-GCTGAGCGCTTTTCTGATC CT-3; SEQ ID NO: 5 | 5-CGAGTGTGCTGCAGGTAGA CA-3; SEQ ID NO: 6 |

Figure 4:
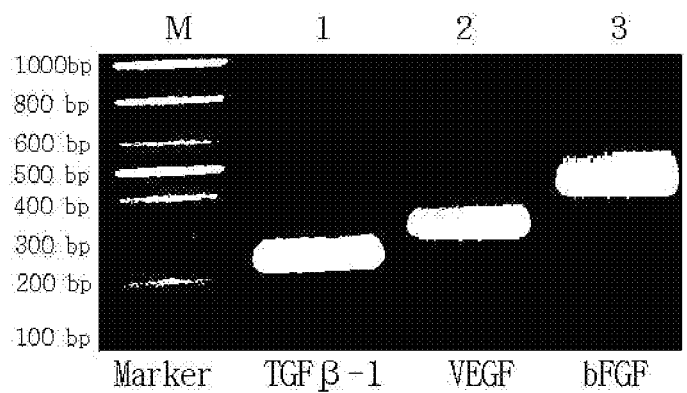
FIG. 4 is an electrophoresis image of TGF β-1, bFGF and VEGF RT-PCR amplification products from adipose-derived stem cells, confirming the expression of TGF β-1, bFGF and VEGF RT-PCR.

As a result, a 482-bp bFGF product (1522 bp-2003 bp) corresponding to SEQ ID NO: 7, a 343-bp VEGF product (1080 bp-1422 bp) corresponding to SEQ ID NO: 8, and a 212-bp TGF β-1 product (2119 bp-2330 bp) corresponding to SEQ ID NO: 9, identified the expression of growth factors in the adipose-derived stem cells (see FIG. 4).

Also, in order to examine whether growth factors are present in a culture medium, an enzyme-linked immunosorbent assay was performed.

Specifically, 1 ml of the culture medium obtained by culturing adipose-derived stem cells to passage 3 in the conditions of Example 1-2 was centrifuged at 1200 g for 5 minutes, and then filtered through a 0.22 mm filter to remove cell residue. The filtrate was serially diluted to determine optimal conditions in which a non-specific reaction did not occur. Then, the concentration of each of growth factors VEGF, bFGF and TGF β-1 secreted in the culture medium was measured using a sandwich ELISA kit (Quantikine Human FGF basic Immunoassay, R&D systems).

To examine the concentrations of optimally diluted growth factors, the culture medium was serially diluted at the same concentration ratio with a calibration dilution in the kit, the concentration at the absorbance included in the range of the standard curve was determined, and the values included in the range of the standard curve were plotted as data. 100 ml of each growth factor-containing culture media and standard solutions of growth factors was placed in each well coated with an antibody to each of the growth factors (Quantikine Human FGF basic Immunoassay, R&D systems) and was cultured at room temperature for 2 hours. After completion of the antigen-antibody binding reaction, each well was washed four times with wash buffer, and 200 ml of a solution (Quantikine Human FGF basic Immunoassay, R&D systems), containing a secondary antibody to each of the growth factors, was placed in each well, followed by culture at room temperature for 2 hours. After completion of the second antibody binding reaction, each well was washed four times with wash buffer, 200 ml of a color-developing reagent (tetramethylbenzidine, R&D systems) was added to each well, and then the absorbance of the medium was measured at 450 nm with an ELISA reader.

Figure 5:
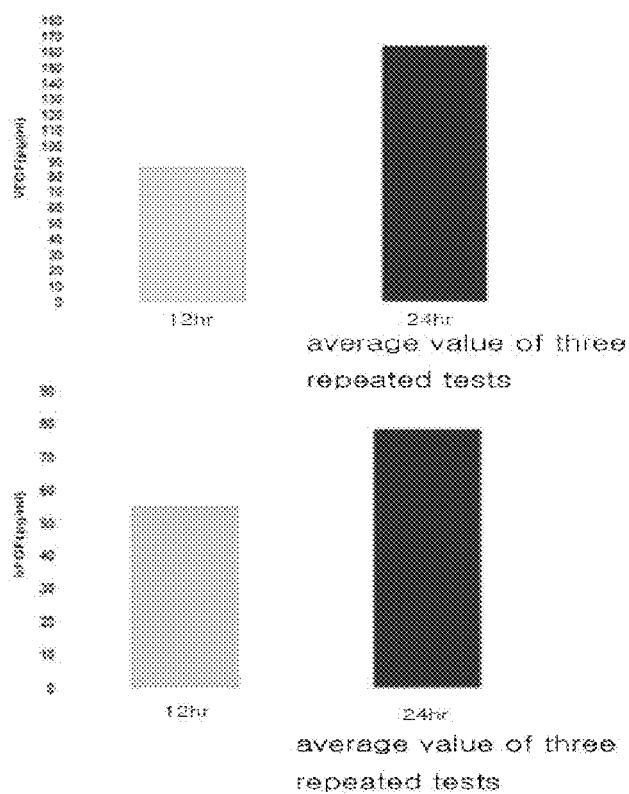
FIG. 5 is a graphic diagram showing the concentrations of bFGF and VEGF secreted in culture media during the culture of adipose-derived stem cells.

As a result, bFGF protein levels showed an increase of 54.96 pg/ml after 12 hours and an increase of 76.393 pg/ml after 24 hours, and VEGF protein levels showed an increase of 87.021 pg/ml after 12 hours and an increase of 163.52 pg/ml after 24 hours (see FIG. 5).

EXAMPLE 3

Activity of Adipose-derived Stem Cells on Collagen Production of Fibroblasts

One of the causes of formation of skin wrinkles is a lack of collagen. Collagen is a major protein of skin dermis and serves to maintain the skin structure and firmness. It is known that the production of collagen decreases as age increases, and the degradation thereof also increases to induce the collapse of the dermal layer, thus producing skin wrinkles. Thus, the effect of a substance for anti-wrinkles activity can be proven by testing the production and degradation of collagen.

(3-1) Coculture of Adipose-derived Stem Cells and Fibroblasts

The effect of adipose-derived stem cells on the collagen production of fibroblasts was estimated through the coculture of adipose-derived stem cells and fibroblasts. In the test, an increase in the production of collagen in fibroblasts, when adipose-derived stem cells were cocultured with fibroblasts in a transwell insert (Costar, Corning), was compared with the production of collagen in the single culture of fibroblasts.

a) Coculture

Fibroblasts (primary cell line) were obtained by finely cutting a portion of human skin tissue (Department of Laboratory Medicine, Hangang Sungsim Hospital; 9 years old; circumcison fragment) suspended in PBS, stirring the cut tissue with 50-100 ml of trypsin for 20 minutes, centrifuging the stirred tissue, and then filtering the tissue through a 7-mm nylon filter.

The filter cell suspension was seeded on the bottom of a culture dish and a DMEM medium containing penicillin (100 IU/mL), streptomycin (100 g/mL) and 10% FBS was added. Then, the cells were cultured in an incubator containing 5% carbon dioxide at 37° C. The fibroblasts, which reached a confluence of 80%, were dispensed into a 6-well plate at a density of $5 \times 10^4$/well and cultured for 24 hours in the same culture conditions as in the subculture process.

The adipose-derived stem cells isolated in Example (1-1) were cultured in a transwell insert for 24 hours in the same conditions as the case of the fibroblasts, and then the transwell insert was inserted into the 6-well plate in which the fibroblasts were being cultured. The stem cells and the fibroblasts were cocultured in the 6-well plate. At this time, the medium below the transwell insert was discarded, the 6-well plate was washed with PBS, a fresh medium was added thereto, and the fibroblasts and the adipose-derived stem cells were cocultured.

1 ml of the cocultured medium was taken at 24 hours and 72 hours after the culture, and the amount of collagen in the culture medium was measured.

In a control group test, fibroblasts, which reached confluence, were dispensed into a 6-well plate at a density of $5 \times 10^4$ cells/well, and then cultured for 24 hours. A transwell insert having no adipose-derived stem cell seeded therein was inserted into the 6-well plate.

b) Analysis of Activity for Collagen Production

1) Measurement of Amount of Collagen by Enzyme-Linked Immunosorbent Assay (ELISA)

The measurement of the amount of collagen was performed using a Procollagen type I peptide EIA kit (TAKARA BIOMEDICAL Co.). 100 ml of an antibody-PoD conjugate solution was placed in each well. Then, 20 μl of fibroblasts, which were optimally diluted with a calibration dilution so as to be included in a collagen standard curve, and 20 μl of fibroblasts cocultured with adipose-derived stem cells, were placed in each well and left to stand at 37° C. for 3 hours. Then, each well was washed four times with wash buffer, and 100 μl of a color-developing reagent was added to each well, followed by culture at room temperature for 15 minutes. Then, the absorbance of the culture medium was measured at 450 nm with an ELISA reader.

2) Measurement of Amount of Collagen in Cells by Semi-Quantity PCR

The total RNA of fibroblasts cocultured with stem cells was extracted using a RNeasy plus mini kit (QIAGEN), and 3 μg of the extracted RNA was amplified by PCR in a reaction solution containing 200 unit MMLV-reverse transcriptase (Promega), 50 mM Tris-HCl (pH 8.3), 75 mM KCl, 3 mM $MgCl_2$, 10 mM DTT, 10 mM dNTP, 25 unit RNase inhibitor and 20 pmole Oligo-dT. The PCR reaction was performed in a T-GRADIENT (BIOMETRA) thermocycler at 37° C. for 45 minutes, and then the MMLV-reverse transcriptase was inactivated at 65° C. for 15 minutes. Specific base sequences for the detection of collagen I type (GenBank No. NM-000089) were constructed based on base sequences recorded in the NCBI Genbank and are shown in Table 3 below.

TABLE 3

| Specific base sequences for detection of collagen type I | | |
|---|---|---|
| | Forward primer | Reverse primer |
| Collagen type I | 5'-CCCTCAAGGTTTC CAAGGAC-3'; SEQ ID NO: 10 | 5'-ACCAGGTTCAC CCTTCACAC-3'; SEQ ID NO: 11 |

Figure 6:
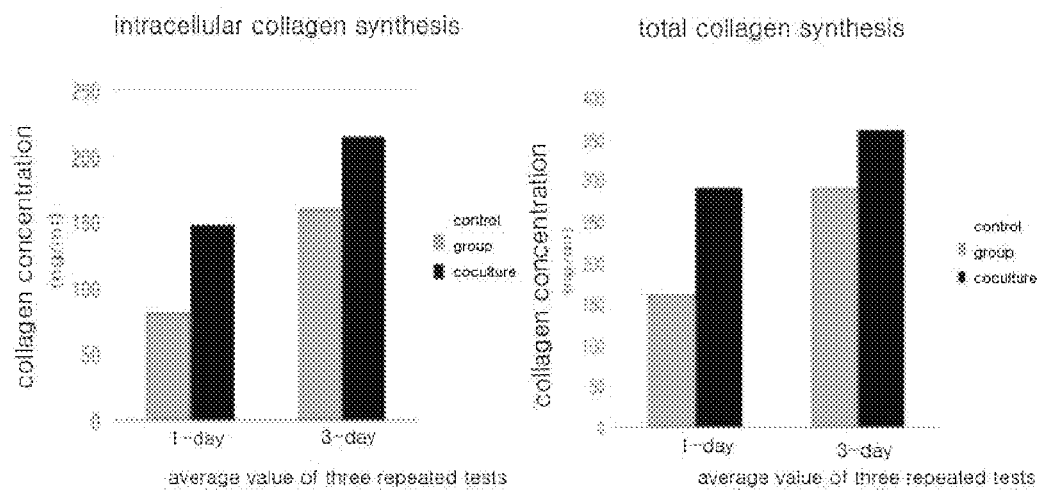
FIG. 6 is a graphic diagram showing the measured collagen synthesis of fibroblasts in mixed culture of fibroblasts and adipose-derived stem cells.

As a result, as shown in FIG. 6, the amount of intracellular collagen synthesis was increased 2.17 times in 1-day culture and 1.27 times in 3-day culture, compared to the control group, and the amount of total collagen synthesis was increased 1.44 times in 1-day culture and 1.14 times in 3-day culture.

(3-2) Collagen Synthesis of Fibroblasts by Adipose-derived Stem Cell Culture Medium In order to examine the effect of a culture medium (conditioned medium) of adipose-derived stem cells on the collagen synthesis of fibroblasts, western blot analysis (specific protein detection) was performed.

To collect a culture medium of adipose-derived stem cells, 5×10$^5$ adipose-derived stem cells were seeded into a T75 flask after subculture. Herein, serum-free DMEM was used as the medium. The cells were cultured in a 5% $CO_2$ incubator at 37° C. for 3 days, and then the medium was harvested and filtered through a 0.22-um syringe filter. The filtrate was used as a serum-free conditioned medium in the following test.

Fibroblasts were subcultured, and then seeded into a 0.1% FBS-containing DMEM in a 6-well plate at a density of 5×10$^4$ cells/well. After the cells were cultured for 24 hours, the medium was replaced with the above-described serum-free conditioned medium. For the control group, serum-free DMEM was used. After 12 hours, serum was adjusted to 2%, and after 30 hours of culture, the culture medium was harvested and subjected to western blot analysis.

The electrophoresis of the culture medium was performed according to the SDS-PAGE method using an electrophoresis kit (Bio-rad). In the electrophoresis, 8% polyacrylamide gel was used and transferred to a PVDF membrane (Bio-rad). Then, the blot was blocked with a 5% nonfat dry milk-containing TBST (50 mM Tris, pH8.0, 138 mM NaCl, 2.7 mM KCl, and 0.1% (w/v) Tween 20). The medium was allowed to react overnight with antibody collagen type I (Santacruz) as a primary antibody and allowed to react with peroxidase-Rabbit anti-goat IgG (Zymed) as a secondary antibody for 30 minutes. Finally, the medium was allowed to react with an antibody detection reagent (ECL, Milipore) for 1 minute, and the test results were observed.

Figure 16:
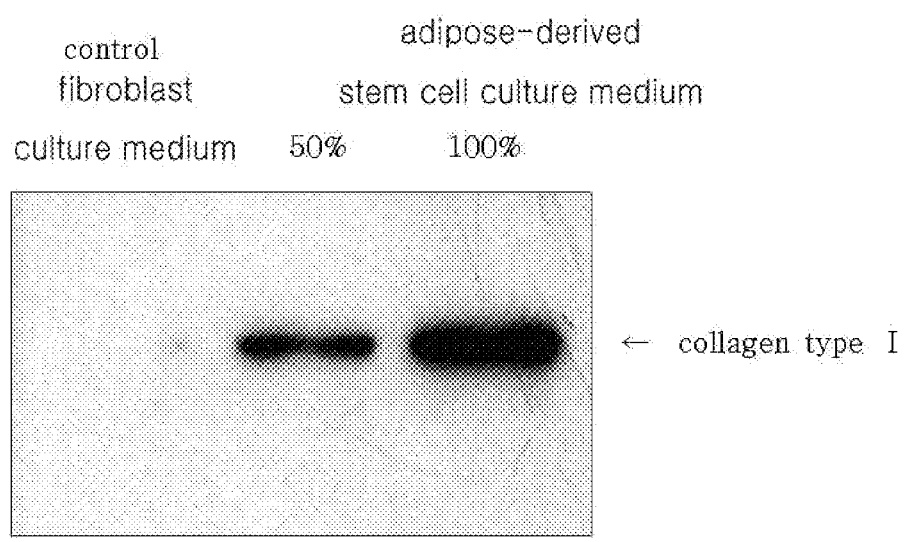
FIG. 16 is a photograph showing the results of Western blot analysis for the collagen synthesis of fibroblasts, in adipose-derived stem cell culture media.

As a result, as shown in FIG. 16, the adipose-derived stem cell culture medium treated with fibroblasts showed an increase of more than 2 times the amount of collagen compared to the medium untreated with fibroblasts (quantified with a gene tool software; 2.16-fold increased). This demonstrates that the culture medium of adipose-derived stem cells increases the collagen synthesis of fibroblasts, and thus suggests that the culture medium of adipose-derived stem cells can be used as an anti-wrinkle substance for preventing skin aging.

EXAMPLE 4

Stimulation of Fibroblast Proliferation by Adipose-derived Stem Cells

Stem cells isolated from adipose tissue were cultured to passage 3 as described in Example (1-2), and then 10$^6$ cells of the stem cells were seeded into a T175 flask (area: 175 cm$^2$; and volume: 500 ml) and cultured for 3 days. The stem cell culture medium was collected, and added to concentrations of 10%, 25%, 50% and 100% to a 6-well plate, in which passage-4 fibroblast cells from the skin tissue of a 9 year old boy (Department of Laboratory Medicine, Hangang Sungsim Hospital; 9 years old; circumcison fragment) were dispensed at a density of 25,000 cells/well.

After 3 days, the proliferation of the fibroblasts was measured with a cell viability measurement kit (cell counting kit-8, Dojindo Molecular Technologies, Inc.), and then the absorbance of the cells was measured at 450 nm with an ELISA reader.

Figure 7:
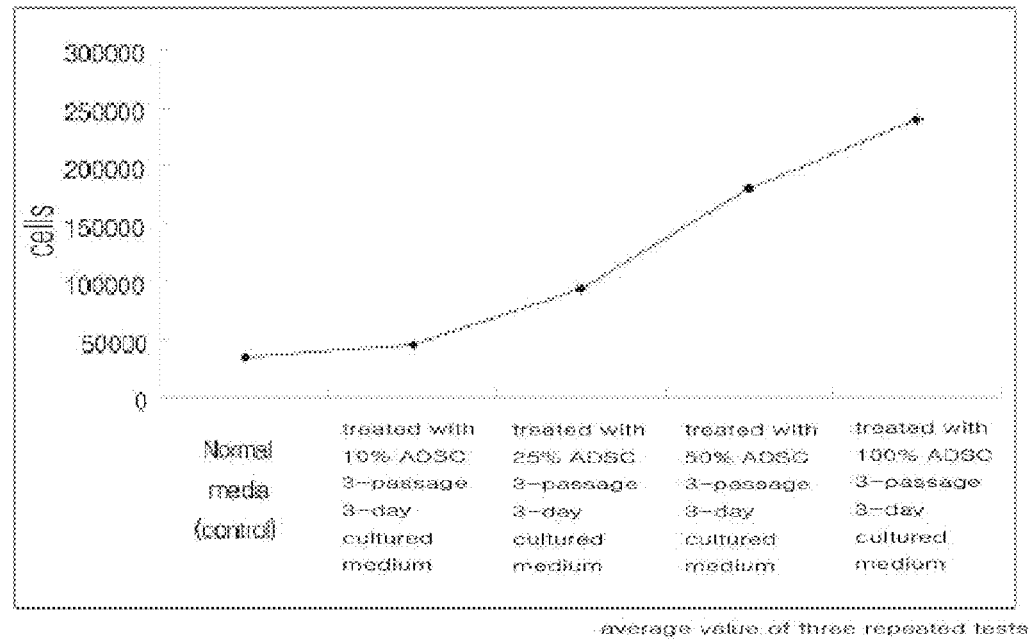
FIG. 7 is a graphic diagram showing the number of fibroblast cells in varying concentrations of adipose-derived stem cell culture media.
Figure 8:
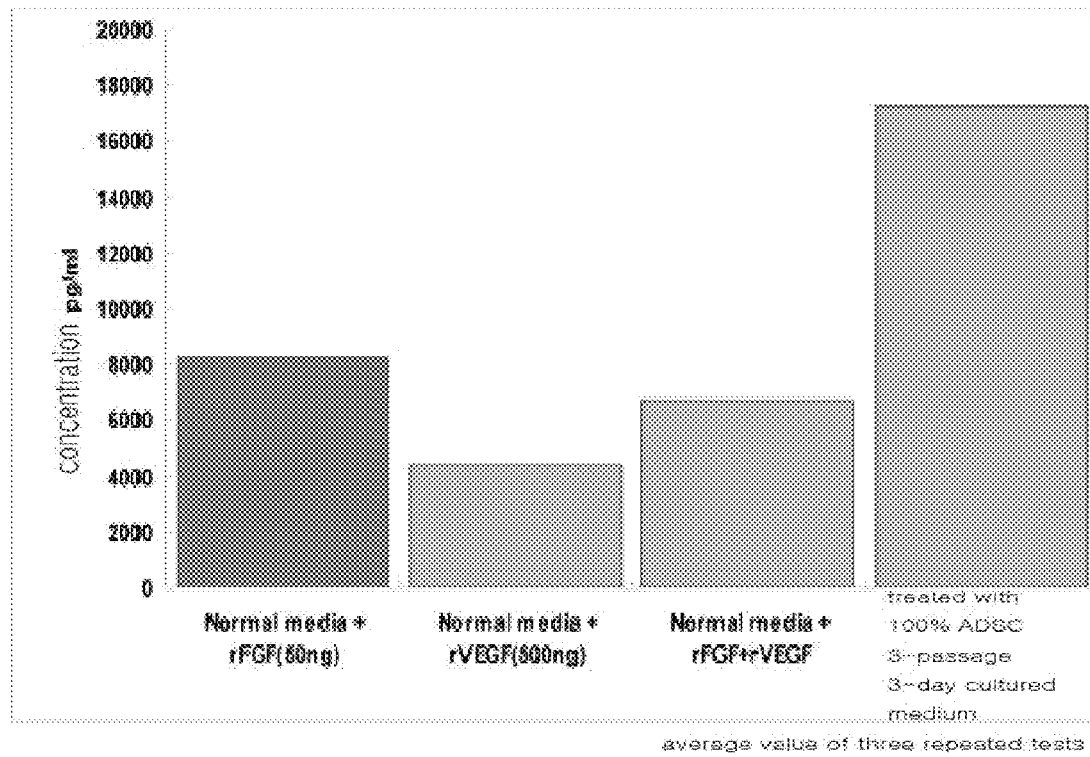
FIG. 8 is a graphic diagram showing the comparison of cell proliferation potential between adipose-derived stem cell culture media and recombinant growth factor-containing media.

As a result, as shown in Table 4, it was demonstrated that the growth factors secreted from the adipose-derived stem cells stimulated the proliferation of fibroblasts. Also, it was observed that the proliferation of fibroblasts was stimulated as the concentration of growth factors secreted from adipose-derived stem cells was increased (see FIG. 7).

TABLE 4

Number of fibroblast cells in varying concentrations of culture media containing growth factors secreted from adipose-derived stem cells

| Classification | Cells |
| --- | --- |
| Normal media (control group) | 35000 |
| Treated with 10% ADSC 3-passage 3-day cultured medium | 45000 |
| Treated with 25% ADSC -3passage 3-day cultured medium | 93000 |
| Treated with 50% ADSC 3-passage 3-day cultured medium | 180000 |
| Treated with 100% ADSC 3-passage 3-day cultured medium | 240000 |

EXAMPLE 5

Comparison of Growth Factors Secreted from Adipose-derived Stem Cells with Recombinant Growth Factors Expressed in *E. Coli*

Stem cells isolated from adipose tissue were cultured to passage-3 as described in Example (1-2), and then 10$^6$ cells of the stem cells were seeded into a T175 flask (area: 175 cm$^2$; volume: 500 ml) and cultured for 3 days. The culture medium was collected, and added at a concentration of 100% to a 6-well plate in which passage-4 fibroblast cells from the skin tissue of a 9 years old boy were dispensed at a density of 5000 cells/well. For the control group, a medium containing the same concentrations of recombinant growth factors VEGF and bFGF (Santa Cruz.) expressed in *E. coli* was used. Cell proliferation potential was compared between the adipose-derived stem cell culture medium and the recombinant growth factor-containing culture medium using a cell viability measurement kit.

As a result, when the growth factors obtained by the overexpression and isolation of growth factor genes in *E. coli* using the genetic recombinant method were compared with the growth factors synthesized from the adult stem cells, it was demonstrated that the growth factors synthesized from the adipose-derived adult stem cells had excellent effects compared to the growth factors obtained by the existing synthesis method. The results are shown in Table 5 below.

TABLE 5

Comparison of cell proliferation potential between adipose-derived stem cell culture media and recombinant growth factor-containing media

| Classification | Cells |
| --- | --- |
| Normal media + rFGF (50 ng) | 8215.3 |
| Normal media + rVEGF (500 ng) | 4408.9 |
| Normal media + rFGF + rVEGF | 6727.1 |
| Treated with 100% ADSC 3-passage 3-day cultured medium | 17215 |

EXAMPLE 6

Culture Method of Adipose-derived Stem Cells Having Increased Growth Factor Secretion (6-1) Physical Stimulation Adipose tissue-derived stem cells were cultured to passage 3 as described in Example (1-2), and when the cultured cells reached a confluence of 80%, the cells were collected with trypsin/EDTA. Then, the cells were accurately dispensed into a 6-well plate at a density of 25,000 cells/well.

24 hours after the dispense, when the cells were all attached, the culture medium was completely removed, and the cells were a multigas incubator containing 5% carbon dioxide and 1% oxygen in physical conditions, and was irradiated with an energy of 90 mJ/cm$^2$ at a wavelength of 280-320 nm (model BEX-800; Ultra-Lum, Inc.) corresponding to UV B. In a nutrient deficiency reaction, the cells were cultured in Dulbecco's phosphate buffered saline containing Mg$^{2+}$ and Ca$^{2+}$ for a maximum of 4 hours immediately until the cells were precipitated, and then, the medium was replaced with the serum-free medium of Example (1-2). In scratch stimulation using mechanical friction, the cells attached to a surface of culturing vessel were scratched with a blade in the form of a lattice having a size of 1 mm×1 mm.

(6-2) Chemical Conditions

To the serum-free medium of Example (1-2), prepared by adding a Ham's F-12 nutrient mixture to DMEM, which did not contain a pH indicator such as phenol red, at a ratio of 1:1, and adding thereto 2 mM L-glutamine, 1 mM sodium pyruvate and 0.17% sodium bicarbonate, vitamins A, B, C and D at effective levels that did not cause cytotoxicity. Cells were cultured in this medium.

The cells were cultured in the above medium in a 5% carbon dioxide incubator at 37° C. for more than 48 hours, and then 200 µl of the culture medium supernatant was centrifuged at 3,000 rpm and filtered through 0.22-µm filter paper. Then, the concentrations of bFGF, VEGF and TGF β-1 in the filtrate were measured by the enzyme-linked immunosorbent assay (ELISA) of Example 2.

In the analysis results, the optimal concentration of vitamin A was 2-10 µM, the optimal concentration of vitamin B2 was 50-100 µM, the optimal concentration of vitamin C was 10-100 µM, and the optimal concentration of vitamin D was 5-10 µM. It was seen by MTT assay that, no cytotoxicity occurred at such concentrations, and the synthesis of each of the growth factors targeted in the present invention was increased.

(6-3) Culture Conditions of Control Group

As a control group, a normal medium, was used, which was not subjected to physical stimulation or chemical stimulation. The increase in growth factors was compared between the control group and the culture medium subjected to physical stimulation and chemical stimulation.

In a culture process, cells were added to a serum-free medium prepared by adding a Ham's F-12 nutrient mixture to DMEM not containing a pH indicator such as phenol red, at a ratio of 1:1, and adding thereto 2 mM L-glutamine, 1 mM sodium pyruvate and 0.17% sodium bicarbonate. Then, the cells were cultured in a 5% carbon dioxide incubator at 37° C. for more than 48 hours. Then, 200 µl of the culture medium supernatant was centrifuged at 3,000 rpm, and then filtered through 0.22-µm filter paper. Then, the concentrations of bFGF, VEGF and TGF β-1 were measured by the enzyme-linked immunosorbent assay (ELISA) of Example 2.

(6-4) Combination of Stimulations

The case where physical stimulation is used in combination with chemical stimulation will now be described. For bFGF, UV light was irradiated into a culture medium, and then immediately the medium was replaced with a DMEM medium containing a Ham's F-12 nutrient mixture and optimized concentrations of 2 µM vitamin A, 50 µM vitamin B, 10 µM vitamin C and 10 µM vitamin D. The medium was cultured at low-oxygen stimulation conditions of 1% oxygen and 5% carbon dioxide for 48 hours.

For VEGF, a medium was irradiated with UV light and then subjected to scratch stimulation. Immediately after this, the medium was replaced with a DMEM medium containing a Ham's F-12 nutrient mixture and optimized concentrations of 2 µM vitamin A, 50 µM vitamin B, 10 µM vitamin C and 10 µM vitamin D. The medium was cultured low-oxygen stimulation conditions of 1% oxygen and 5% carbon dioxide for 48 hours.

For TGF β-1, a medium was irradiated with UV light and then subjected to scratch stimulation and nutrient deficiency stimulation. Then, the medium was replaced with a DMEM medium containing a Ham's F-12 nutrient mixture and optimized concentrations of 2 µM vitamin A, 50 µM vitamin B, 10 µM vitamin C and 10 µM vitamin D. The medium was cultured at low-oxygen stimulation conditions of 1% oxygen and 5% carbon dioxide for 48 hours.

To obtain the highest total amount of bFGF. VEGF and TGF β-1, a medium was irradiated with UV light, and then replaced with a DMEM medium containing a Ham's F-12 nutrient mixture and optimized concentrations of 2 µM vitamin A, 50 µM vitamin B, 10 µM vitamin C and 10 µM vitamin D. The medium was cultured low-oxygen stimulation conditions of 1% oxygen and 5% carbon dioxide for 48 hours.

(6-5) Results

Figure 9:
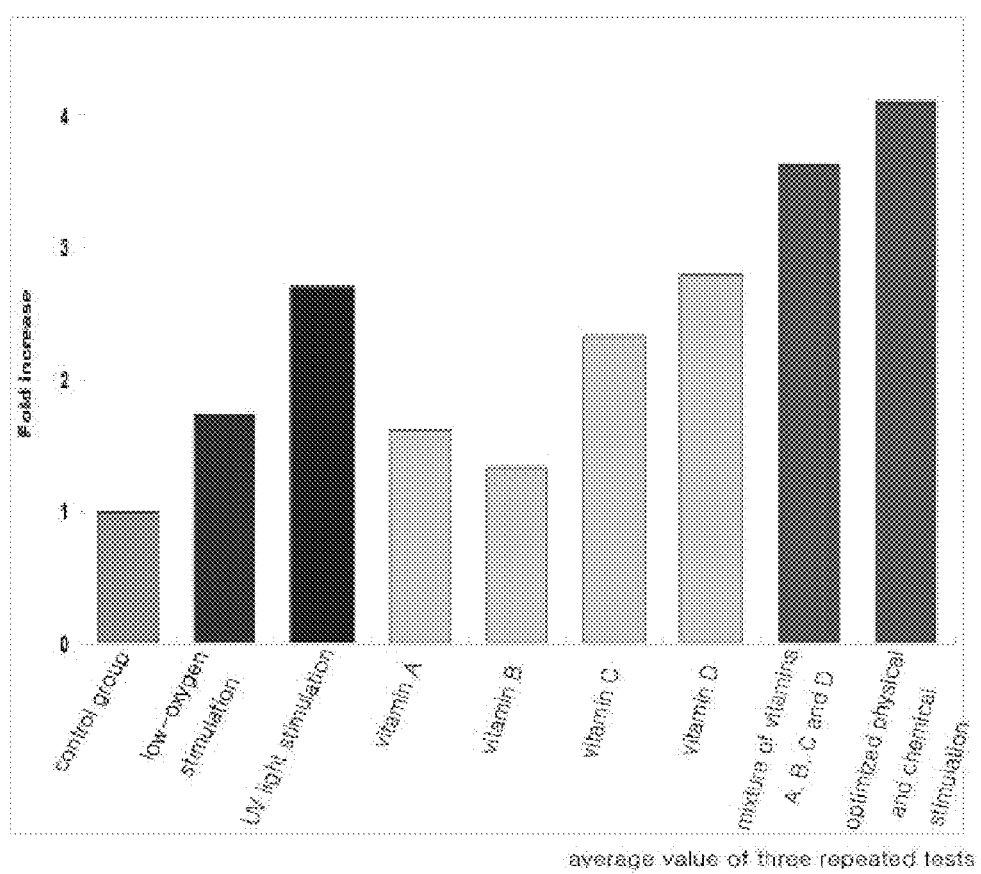
FIG. 9 is a graphic diagram showing the comparison of secretion of a basic fibroblast growth factor (bFGF) of adipose-derived stem cells cultured in physical and chemical conditions according to the present invention.

As shown in FIG. 9, in comparison with the control group, bFGF was increased 1.74 times in the case of low-oxygen stimulation, and 2.71 times in the case of UV light stimulation. In the case of chemical stimulation, bFGF was increased 1.62 times for vitamin A, 1.33 times for vitamin B, 2.33 times for vitamin C and 2.80 times for vitamin D.

When low-oxygen stimulation and UV light stimulation, which among the above stimulations have excellent effects on growth factor expression, were performed in combination, the synergistic effect thereof was shown. In the case of chemical stimulation, bFGF protein levels in a medium containing optimized concentrations of vitamins A, B, C and D were increased 3.62 times. In case where physical stimulation was applied in combination with chemical stimulation, bFGF protein levels were increased 4.11 times, when low-oxygen stimulation was optimized, UV light was irradiated and the concentrations of vitamins A, B, C and D were optimized.

Figure 10:
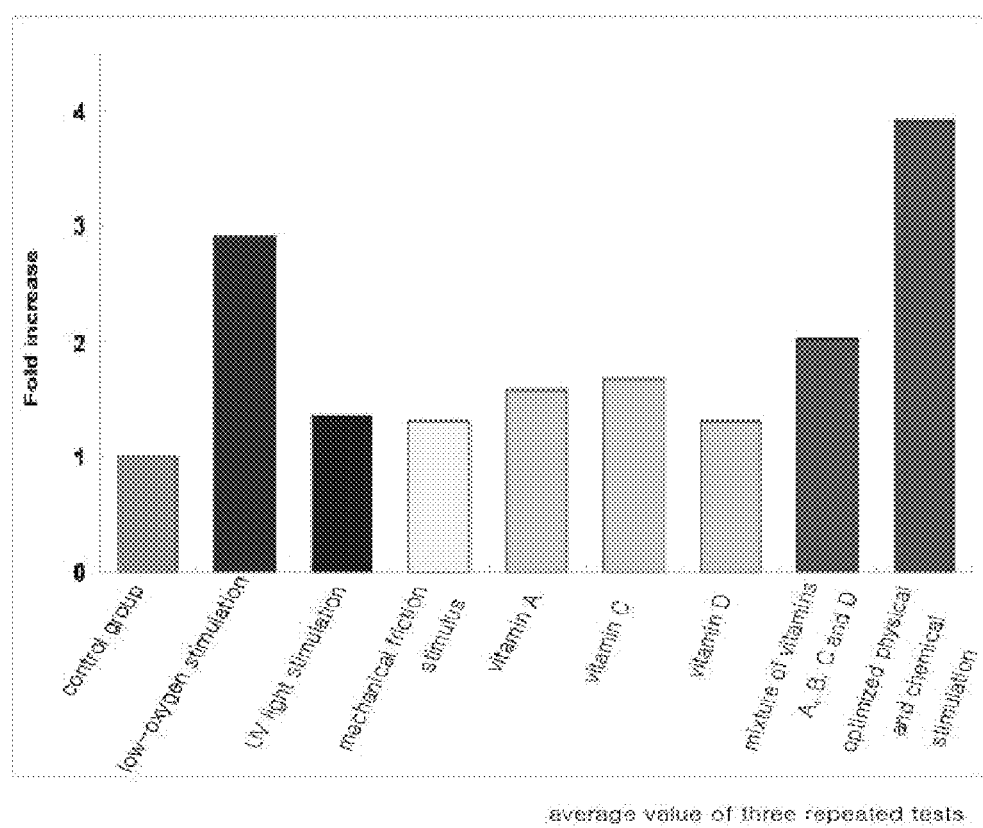
FIG. 10 is a graphic diagram showing the comparison of the secretion of a vascular epithelial growth factor (VEGF) of adipose-derived stem cells cultured in physical and chemical conditions according to the present invention.

As shown in FIG. 10, in comparison with the control group, vascular endothelial growth factor (VEGF) protein levels were increased 2.53 times in the case of low-oxygen stimulation, 1.36 times in the case of UV light stimulation, and 1.33 times in the case of scratch stimulation caused by mechanical friction. In the case of chemical stimulation, VEGF protein levels were increased 1.59 times for vitamin A, 1.56 times for vitamin B, 1.68 times for vitamin C, and 1.30 times for vitamin D.

When low-oxygen stimulation and UV light stimulation, which among the above stimulations have excellent effects, on the expression of growth factors, were performed in combination, the synergistic effect thereof was shown. In the case of chemical stimulation, VEGF protein levels in a medium containing optimized concentrations of vitamins A, B, C and D were increased 2.03 times.

In the case where physical stimulation was applied in combination with chemical stimulation, VEGE protein levels could be increased 3.92 times, when low-oxygen stimulation was optimized, UV light stimulation and scratch stimulation were used and the concentrations of vitamins A, B, C and D were optimized.

Figure 11:
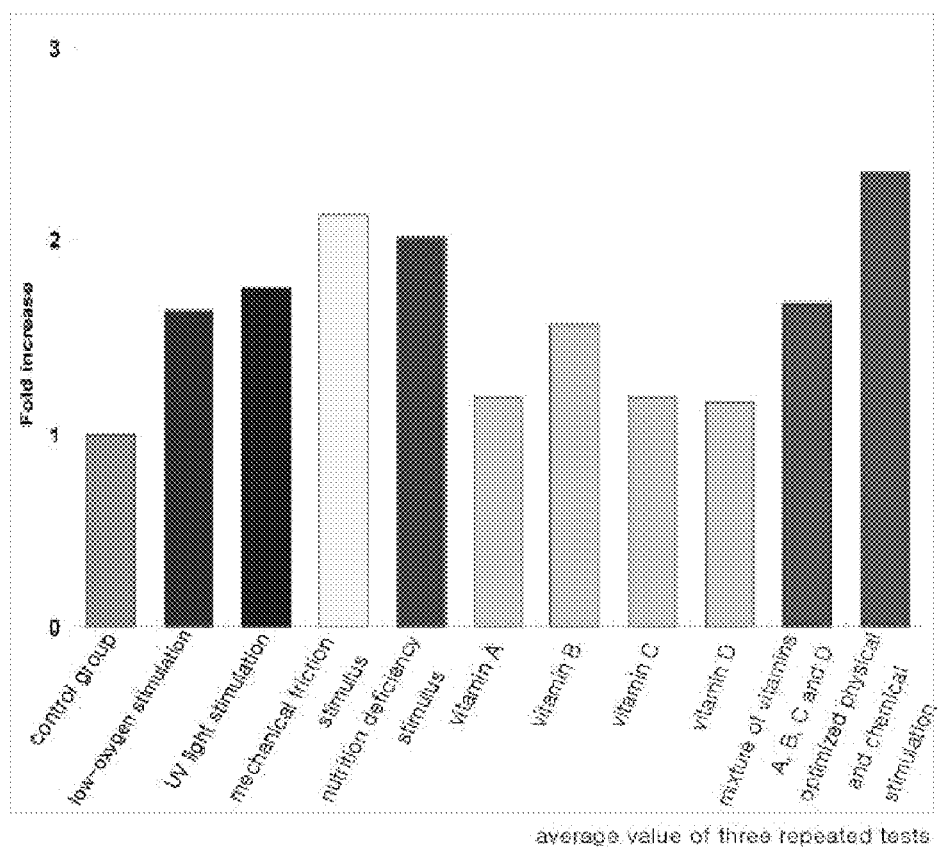
FIG. 11 is a graphic diagram showing the comparison of the secretion of transforming growth factor-beta (TGF-β) of adipose-derived stem cells cultured in physical and chemical conditions according to the present invention.
Figure 12:
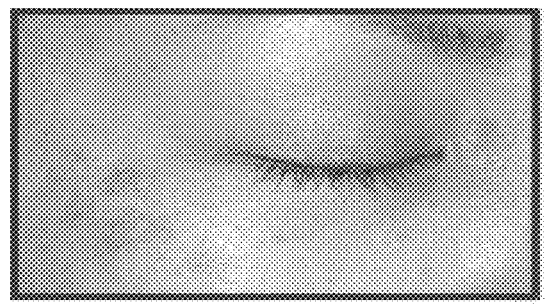
FIGS. 12, 13, 14 and 15 are photographs showing the wrinkle-reducing activity of a composition containing growth factors isolated from autologous adipose-derived adult stem cells.
Figure 12:
Figure 12:
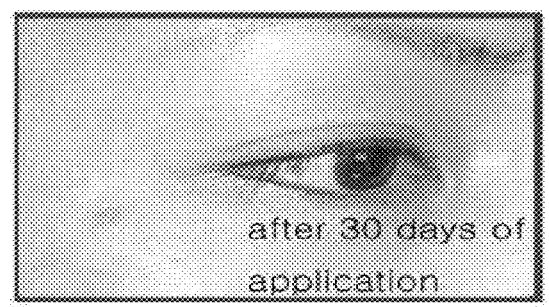
Figure 12:
Figure 12:
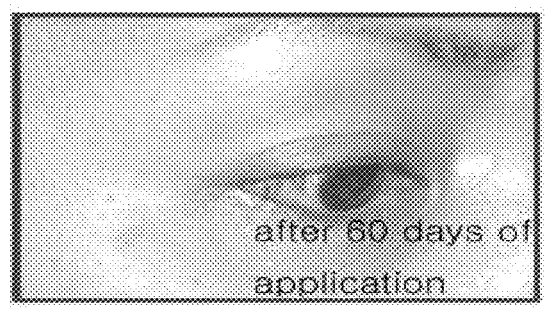
Figure 13:
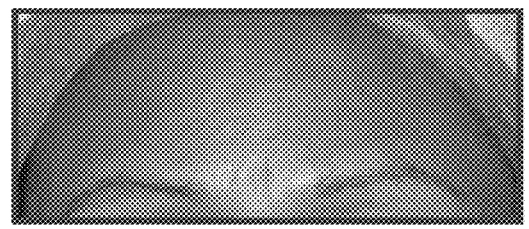
Figure 13:
Figure 13:
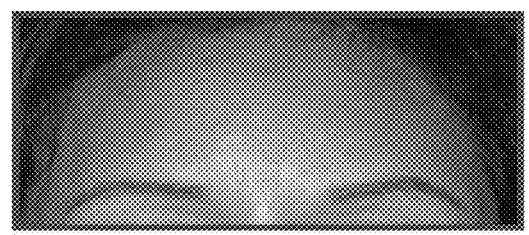
Figure 14:
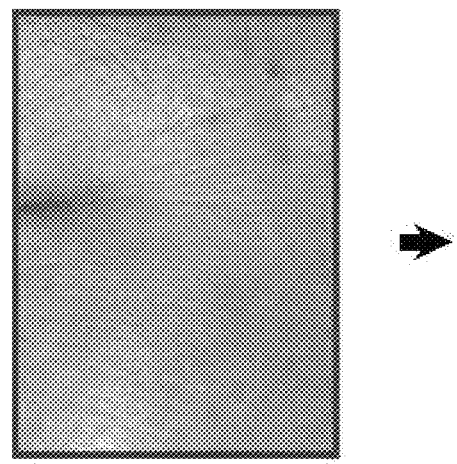
Figure 14:
Figure 14:
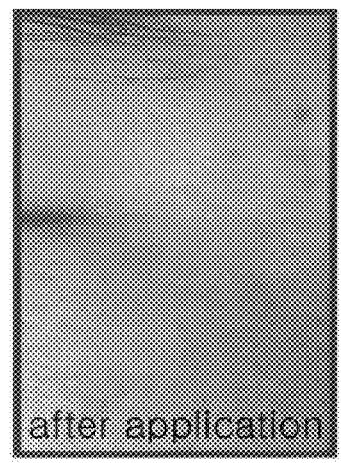
Figure 15:
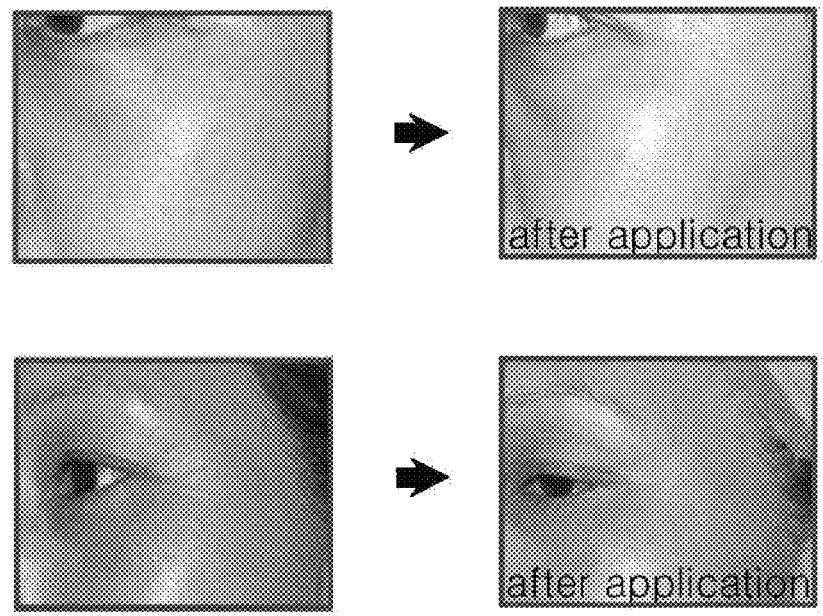

As shown in FIG. 11, in comparison with the control group, transforming growth factor beta-1 (TGF β-1) protein levels were increased 1.64 times in the case of low-oxygen stimulation, 1.75 times in the case of UV light stimulation, 2.13 times in the case of scratch stimulation caused by mechanical friction, and 2.01 times in the case of nutrient deficiency stimulation. In the case of chemical stimulation, TGF β-1 protein levels were increased 1.20 times for vitamin A, 1.56 times for vitamin B, 1.20 times for vitamin C, and 1.16 times for vitamin D.

When low-oxygen stimulation and UV light stimulation, which among the above stimulations have excellent effects, on the expression of growth factors, were performed in combination, the synergistic effect thereof was shown. In the case of chemical stimulation, TGFb-1 protein levels in a medium containing optimized concentrations of vitamins A, B, C and D were increased 1.68 times.

In the case where physical stimulation was applied in combination with chemical stimulation, TGF β-1 protein levels could be increased 2.35 times, when low-oxygen stimulation was optimized, UV light stimulation, scratch stimulation and low-oxygen stimulation were used and the concentrations of vitamins A, B, C and D were optimized.

Also, in order to obtain the highest total amount of bFGF, VEGF and TGF β-1, it is most preferable to subject a medium to low-oxygen stimulation and UV light stimulation and add vitamins A, B, C and D to the medium. Specifically, a medium is irradiated with UV light, and then replaced with a medium containing a Ham's F-12 nutrient mixture and optimized concentrations of vitamins A, B, C and D, and the medium is cultured in a condition of low-oxygen stimulation for the optimized culture time. In this case, bFGF protein levels are increased 4.11 times compared to the control group, VEGF protein levels are increased 3.8 times, and TGF β-1 protein levels are increased 1.9 times.

EXAMPLE 7

Defensive Effect of Adipose-derived Stem Cells Against Exposure of Keratinocytes to UV Light The defensive effect of growth factors secreted from adipose-derived stem cells against the exposure of keratinocytes UV light was tested in the following manner.

Keratinocytes were dispensed into a 6-well plate at a suitable cell concentration in KGM (karatinocyte growth medium; Clonetics.) and incubated in a 5% carbon dioxide incubator at 37° C. To the medium, 2.5 cc of 100% ADSC 3-passage 3-day cultured medium was added to adjust the KGM to 5 cc. Also, 2 uM retinol was added to 5 cc of KGM. Also, as a negative control group, 5 cc of KGM alone was administered to keratinocytes. Each of the test samples was stabilized for 4 hours, such that the raw materials were sufficiently dispersed. After that, each of the test samples was irradiated with UV light using a 40 W double lamp for 8 minutes in an aseptic laboratory. After 24 hours, the UV defense function of the test sample was measured by determining the viability of the cells in comparison with the negative control group, which was untreated with the culture medium or retinol and irradiated with UV light for 8 minutes.

As a result, as shown in Table 6 below, the cell group, which was cultured as described in Example (1-2) and contained VEGF, bFGF and TGF β-1, showed a defensive effect of 67%, the cell group administered with retinol showed a defensive effect of 54%, and the negative control group showed a defensive effect of 55%. This indicates that retinol has a low defensive effect against UV lights, whereas the growth factors secreted from adipose-derived stem cells has an increased defensive effect against UV light.

TABLE 6

Measurement results of anti-aging effects

| Tested materials | Defensive effect |
|---|---|
| 100% ADSC 3-passage 3-day cultured medium | 67% |
| Retinol | 54% |
| Negative control group | 55% |

EXAMPLE 8

Effects of Adipose-derived Stem Cell Growth Factors on Skin Photoaging caused by UV Light Irradiation in Nude Mice In order to assess the activity of a culture medium, which was cultured as described in Example (1-2) and contained VEGF, bFGF and TGF β-1, the following test was performed using thirty 15-20-week-old nude mice.

Irradiating the backs of nude mice with UV light at a dose of 2 mJ/cm$^2$ using an UV simulator was performed two times a week for 4 weeks, thus inducing the abnormal hyperkeratinization of the skin. Then, growth factors synthesized by a chemical synthesis method, growth factors produced by a genetic recombination method, and growth factors produced by adipose-derived adult stem cells, were applied on one side of the backs of the nude mice in an amount of 1 cc two times a day for 2 weeks, while the other side was untreated for comparison. After 2 weeks, the anti-aging effects of the growth factors were observed visually and assessed (Jin Ho Chung et al. Archives of Dermatology, 137-8 (2001)). The measurement results are shown in Table 7 below.

TABLE 7

Measurement results of anti-aging effects

| | Remarkable effect (number of mice) | Moderate effect (number of mice) | No effect (number of mice) |
|---|---|---|---|
| 100% culture medium | 23 | 7 | 0 |
| Negative control group | 4 | 8 | 18 |

When each of the growth factors was applied to the nude mice whose aging was artificially induced, the growth factors synthesized from adipose-derived adult stem cells showed the effect of reducing abnormal skin hyperkeratinization in all of the 30 animals, and this effect was excellent compared to that of the growth factors synthesized by the chemical synthesis method or the genetic recombination method.

EXAMPLE 9

Anti-wrinkle Effect of Growth Factors Secreted from Autologous Adipose-derived Stem Cells in Human Beings In order to verify the wrinkle-reducing effect of growth factors synthesized from adipose-derived adult stem cells on 30-50-years old women, 20 persons per test group were selected and the following test was conducted.

1 cc of a adipose-derived stem cell culture medium purified to have a VEGF content of 30 ng, a bFGF content of 30 ng and a TGF β-1 content of 70 ng was applied on the brow or around one eye of each of the women subjects two times a day for 8 weeks, and a negative control group (1 cc of physiological saline as a basic solution) was applied around the other eye for comparison.

After 4 weeks and 8 weeks, the wrinkle-reducing effect of the test sample was visually observed and the measurement results are summarized in Table 8 below.

TABLE 8

Measurement results

| | Remarkable effects (number of persons) | Moderate effects (number of persons) | No effect (number of persons) |
|---|---|---|---|
| Growth factor-containing culture medium | 8 | 12 | 0 |
| Negative control group | 2 | 4 | 14 |

As can be seen from the results of Table 8 and FIGS. 12 to 15, the application of the growth factors synthesized from adult stem cells showed an excellent wrinkle-reducing effect.

[Industrial Applicability]

The human growth factors produced according to the method of the present invention are substances having secured stability and physiological activity, and thus can be used to develop drugs, quasi drugs, cosmetics and the like for anti-wrinkles, wound healing, and scar removing.

Also, the adipose-derived stem cell culture medium according to the present invention contains various growth factors in large amounts, and thus can be used by themselves in drugs, quasi drugs, cosmetics and the like for anti-wrinkles, wound healing, and scar removal.

[Sequence List Text]

SEQ ID NOS: 1-6 and 10-11 according to the present invention are amplification primer pairs for the detection of specific proteins, and SEQ ID NOS: 7-9 are amplification products encoding human growth factors.

The invention claimed is:

1. A method for producing medium containing a basic fibroblast growth factor (bFGF), comprising the steps of:
   (i) isolating adult stem cells from mammalian adipose tissue;
   (ii) culturing said cells in a serum medium, and then subculturing said cells in a serum-free medium; and
   (iii) irradiating said cells with UV light, replacing the medium with a medium containing optimized concentrations of vitamins A, B, C and D, and then culturing said cells in the replaced medium in a condition of low-oxygen stimulation at 1-5% $O_2$,
   wherein the medium contains bFGF secreted from the adult stem cells.

2. A method for producing medium containing a vascular endothelial growth factor (VEGF), comprising the steps of:
   (i) isolating adult stem cells from mammalian adipose tissue;
   (ii) culturing said cells in a serum medium, and then subculturing said cells in a serum-free medium; and
   (iii) irradiating said cells with UV light, applying a scratch stimulation to said cells, replacing the medium with a medium containing optimized concentrations of vitamins A, B, C and D, and then culturing said cells in the replaced medium in a condition of low-oxygen stimulation at 1-5% $O_2$,
   wherein the medium contains VEGF secreted from the adult stem cells.

3. A method for producing medium containing human growth factors, comprising the steps of:
   (i) isolating adult stem cells from mammalian adipose tissue;
   (ii) culturing said cells in a serum medium, and then subculturing said cells in a serum-free medium; and
   (iii) irradiating said cells with UV light, replacing the medium with a medium containing optimized concentrations of vitamins A, B, C and D, and then culturing said cells in the replaced medium in a condition of low-oxygen stimulation at 1-5% $O_2$,
   wherein the medium contains human growth factors secreted from the adult stem cells.

* * * * *